(12) United States Patent
Bunger et al.

(10) Patent No.: US 7,358,278 B2
(45) Date of Patent: *Apr. 15, 2008

(54) CELLULAR PHOSPHORYLATION POTENTIAL ENHANCING COMPOSITIONS PREPARATION AND USE THEREOF

(76) Inventors: Rolf Bunger, 1922 Kenbar Ct., McLean, VA (US) 22101; Ajay Verma, 14226 Reed Farm Way, North Potomac, MD (US) 20878

( * ) Notice: Subject to any disclaimer, the term of this patent is extended or adjusted under 35 U.S.C. 154(b) by 409 days.

This patent is subject to a terminal disclaimer.

(21) Appl. No.: 10/643,080

(22) Filed: Aug. 19, 2003

(65) Prior Publication Data

US 2004/0147604 A1 Jul. 29, 2004

Related U.S. Application Data

(60) Continuation-in-part of application No. 09/828,589, filed on Apr. 9, 2001, now abandoned, which is a continuation-in-part of application No. 09/550,047, filed on Apr. 14, 2000, now abandoned, which is a continuation-in-part of application No. 08/999,767, filed on Oct. 27, 1997, now abandoned, which is a continuation of application No. 08/643,284, filed on May 8, 1996, now abandoned, which is a continuation-in-part of application No. 08/646,572, filed on May 8, 1996, now Pat. No. 5,714,515, which is a division of application No. 08/239,635, filed on May 9, 1994, now Pat. No. 5,536,751.

(51) Int. Cl.
*A61K 31/19* (2006.01)
*A61K 31/20* (2006.01)
*A23G 3/20* (2006.01)

(52) U.S. Cl. .................. 514/557; 514/558; 514/559; 514/560; 426/103

(58) Field of Classification Search .................. 514/557
See application file for complete search history.

(56) References Cited

U.S. PATENT DOCUMENTS 5,536,751 A * 7/1996 Bunger .................. 514/557
5,714,515 A * 2/1998 Bunger .................. 514/557

* cited by examiner

*Primary Examiner*—Shelley A. Dodson
(74) *Attorney, Agent, or Firm*—Werten F. W. Bellamy; Pinnacle Technology Group

(57) ABSTRACT

A pharmaceutical composition comprising as an active phosphorylation potential enhancing substance a pharmaceutically-acceptable salt of an alpha-keto carboxylic acid thereof alone or in combination with nicatinamide and creatine and, its use and products containing the same.

19 Claims, 13 Drawing Sheets

CELLULAR PHOSPHORYLATION POTENTIAL ENHANCING COMPOSITIONS PREPARATION AND USE THEREOF

RELATED CROSS REFERENCES

This is a continuation in part of U.S. patent application Ser. No. 09/828,589, filed Apr. 9, 2001 now abandoned, which in turn is a continuation in part of U.S. patent application Ser. No. 09/550,047, filed Apr. 14, 2000 now abandoned, which in turn is a continuation in part of U.S. patent application Ser. No. 08/999,767 filed Oct. 27, 1997 now abandoned, which in turn is a continuation of U.S. patent application Ser. No. 08/643,284 filed May 8, 1996, and now abandoned, which in turn is a continuation in part of U.S. patent application Ser. No. 08/646,572 filed May 8, 1996, now U.S. Pat. No. 5,714,515, issued Feb. 3, 1998 which in turn is a divisional of U.S. patent application Ser. No. 08/239,635 filed May 9, 1994, now U.S. Pat. No. 5,536,751.

TECHNICAL FIELD OF INVENTION

This invention relates to the broad field of cell biology, neurology, pharmacology, immunology, physiology and medicine and relates to bioactive compositions comprising a phosphorylation enhancing amount of a salt of an alpha-keto carboxylic acid, such as pyruvate, in combination with an amino acid, nicotinamide and creatine or an amino acid sufficient to prevent the deterioration or promote preservation and restoration of normal cell functions, including protecting the brain and central nervous system against damage due to trauma, ischemia, degenerative diseases, epilepsy and aging, as well as other disorders in which brain energy metabolism is either decreased or over-burdened by oxidative stress, calcium overload, or excessive glutamate neurotransmission. For example the bioactive composition could be comprised of: 1. Pyruvate and a bioactive agent; 2. Pyruvate and/or an aminoacid, nicotinamide and creatine or 3. Pyruvate and/or an aminoacid, nicotinamide, creatine and a bioactive agent.

BACKGROUND OF THE INVENTION

Injury to the nervous system can produce some of the most debilitation health conditions in patients. These conditions or the loss of billions of dollars worth of productivity and the attendant health states can result in excruciating pain, immobility and other forms of human suffering. Currently millions of people throughout the industrialized, developing and undeveloped countries of the world are being adversely affected.

The nervous system is comprised of nerves, ganglia, spinal cord, brain and retina and consists of glial and neuronal cells, which number in the trillions. Neurons are considered the main cell type responsible for the complex functions associated with the nervous system. Neurons require energy in the form of ATP (adenosine triphosphate) to survive and carry out their functions. The production and maintenance of energy supply inside neurons requires a fuel source such as glucose, cofactors and vitamins, oxygen, and an energy buffering system to utilize ATP efficiently. Applicants have discovered that the specific combination of pyruvate as a fuel source, nicotinamide as a precursor of the cofactor NAD and creatine as a neuronal energy buffering agent provides a minimal combination to increase neuronal energy levels. All three of these agents also happen to have additional pharmacological actions, which help protect neurons from a wide variety of injuries. Unexpectedly, the combination of these agents provides a novel synergistic effect which benefits the neurons in combating injurious biochemical events while at the same time raising cellular energy levels. To maximize the delivery of all three agents to the brain we also define a strategy to enhance local brain pyruvate production using orally administered aminoacids.

Over the past 2 decades a wealth of new information has elucidated many of the fundamental biochemical events that mediate cell injury and death during brain insults such as stroke, trauma, epilepsy and during the progression of neurodegenerative diseases such as Parkinson's, Alzheimer's, and Huntington's disease. Several fundamental injury mechanisms, in fact, appear to play a prominent role in all of these diverse clinical conditions (see the attached review for a detailed survey of the role of these mechanisms in traumatic brain injury). Most prominent among the brain injury mechanisms involved in both acute and chronic brain insults or diseases are: a) oxidative stress in which excessive free radicals are produced, b) an overload of calcium inside the cell cytoplasm, and c) glutamate-mediated excitotoxicity. All three of these events compromise neuronal energy supply (see FIG. 1).

SUMMARY OF THE INVENTION

The subject invention relates, in one aspect to pharmaceutical and/or compositions containing as active ingredients thereof (1) a salt of an alpha-ketocarboxylic acid, such as pyruvate alone or in combination with (2) other substances including a mixture of nicotinamide, and creatine which may contain an aminoacid.

A. Oxidative Stress, Calcium Overload, and Glutamate Excitotoxicity Deplete Energy Oxidative stress refers to the relative abundance of free radicals or reactive oxygen species in comparison to antioxidants. Reactive oxygen species, the major oxidants in biological systems, are known to inactivate glycolytic and mitochondrial enzymes and this may account for the metabolic dysfunction seen in many brain diseases. DNA damage by free radicals can also deplete energy levels through the activation of energy consuming repair mechanisms (see FIG. 1 and also detailed discussion below). Calcium is a major regulator of cellular function. Its levels inside cells are kept very low relative to extracellular fluid by energy dependant mechanisms in the plasma membrane, endoplasmic reticulum, and mitochondria. Injury to any of these organelles can lead to calcium overload inside cells. If energy dependant mechanisms cannot remove this calcium, then several destructive enzymes are activated which destroy cellular integrity. Glutamate is the major excitatory neurotransmitter of the brain and stimulates neuronal activity by raising the intercellular calcium level within a physiological range. During both acute and chronic brain insults, an excess of extracellular glutamate leads to cellular calcium overload and also to oxidative stress. Recent developments in neurotoxicology suggest that there are important inter-relationships between excessive glutamatergic neurotransmission, cellular calcium overload, oxidative stress, and energy homeostasis (FIG. 1).

Even though the involvement of free radicals, calcium overload, and excessive glutamate in acute and chronic brain diseases has been known for some time, several strategies aimed to directly reducing or blocking these factors, have not been effective clinically. Large recent traumatic brain injury and stroke trials using the antioxidants superoxide dismutase of Tirilazad have failed to show any clinical benefit. Clinical trials which feature glutamate antagonists or calcium antagonists have also been disappointing in acute and chronic neuronal disorders. Although many such agents show great promise with in vitro and animal models, they have been severely limited by their clinical toxicity and trial after trial focusing on one of these specific mechanism has had to be abandoned.

B. Enhancement of Nervous Tissue Energy Levels as a Therapeutic Target

An alternative approach for treating neuronal diseases may be one that focuses on nervous tissue energy levels as the target for therapy. Indeed, many agents that target several of the neurotoxic events shown in FIG. 1, may in fact exert their "neuroprotective effects" by reducing overall cellular energy demand. Viewed in this context, the goal of clinical therapy for nervous system disease should perhaps be directed towards enhancing nervous tissue energy pools.

The overall premise is that if brain energy homeostasis can be preserved or enhanced, then endogenous neuroprotective mechanisms may reverse or impede free radical injury or other neurotoxic events. It is important to consider that our brains are constantly generating free radicals, our neurons are constantly secreting glutamate and the intercellular calcium levels in our brain cells are constantly changing. These events are continuously kept from becoming neurotoxic by energy requiring mechanisms. But how can we maintain or enhance nervous tissue energy pools in damaged or degenerative brains? One approach would be to inhibit processes, which might consume excessive energy in futile reactions. Recent work has in fact linked glutamate and free radical injury to such reactions (FIG. 1).

C. PARP Inhibition by Nicotinamide Provide Neuroprotection

Free radicals can result in DNA strand breaks leading to the activation of cellular DNA repair enzymes, the most robust of which is poly(ADP-ribose)polymerase (PARP). This nuclear enzyme uses NAD (nicotinamide adenine dinucleotide, a derivative of niacin, or vitamin B3) as a substrate to form long branching chains of poly(ADP-ribose) covalently attached to a number of DNA-associated proteins. This reaction is thought to facilitate the action of DNA repair enzymes under situations of mild DNA damage. With more severe DNA damage, robust PARP activation rapidly depletes cellular NAD. Several enzymes involved in energy metabolism require NAD as a cofactor. Thus excessive PARP activation impedes energy metabolism and ATP production. A role for PARP over-activation has been recently demonstrated in neuronal cell death resulting from stroke, head trauma, and toxin-induced parkinsonism (reviewed in Pieper, Verma etal., 1999). Mice lacking the gene for PARP have much less brain injury following stroke and trauma and are spared from MPTP neurotoxicity, which is a toxin-induced model for Parkinson's disease. The administration of PARP inhibitors such as benzamide or nicotinamide also affords neuroprotection in diverse injury models. These findings suggest an involvement of PARP in the control of brain energy metabolism during neurotoxic insults and suggest that adequate levels of cellular NAD are vital for neurons. It is not clear why an enzyme normally involved in DNA repair should contribute to cell death, but it is clear from studies involving knockout mice that PARP may be dispensable for DNA repair since these animals show no obvious neurological deficits and are in fact less injured by a variety of insults.

Many PARP inhibitors based on structural similarity with nicotinamide are now in development. Of these, nicotinamide itself may in fact represent the best therapeutic option since this PARP inhibitor is also the precursor for NAD synthesis. Thus, nicotinamide is able to replenish NAD levels as well as blocking its depletion by PARP activation.

Adequate NAD level are crucial for cellular metabolism as key steps during glycolysis and oxidative phosphorylation are dependent upon NAD. A reduction of cellular NAD levels would have a major effect on energy homeostasis since it would block glycolysis at the site of action of glyceraldehyde-3-phosphate dehydrogenase (GAPDH), prevent the conversion of lactate into pyruvate, block the mitochondrial utilization of pyruvate via pyruvate dehydrogenase (PDH), and prevent the oxidative metabolism of other mitochondrial NAD-linked substrates (FIG. 2). Nicotinamide also has multiple protective activities other than inhibition of PARP, to include inhibition of inducible nitric oxide synthase, scavenging of free radicals, suppression of major histocompatibility complex class II expression and ICAM-1 expression on endothelial cells, and inhibition of tumor necrosis factor-alpha production.

While blocking PARP with nicotinamide may replenish NAD levels and improve energy metabolism, this action is unlikely to significantly enhance nervous tissue energy pools by itself. NAD is merely a cofactor in metabolism and does not directly provide fuel for ATP synthesis. Its main function is to serve as a cofactor for the key glycolytic enzymes glyceraldehyde-3-phosphate dehydrogenase (GAPDH) and lactate dehydrogenase (LDH), the mitochondrial enzyme complex pyruvate dehydrogenase, as well as other enzymes in the mitochondrial tricarboxylic acid cycle (FIG. 2).

Thus, enhancing brain NAD levels has to be accompanied by an adequate fuel source to have any significant effect on brain energy pools. Indeed the supply of fuel to injured cells in the brain may also be severely compromised since, in addition to neuronal involvement, glia are also frequently damaged in both acute and chronic brain disorders. Efficient brain metabolism requires intricate metabolic cooperation between astrocytes (a specific type of glial cell) and neurons. Astrocytes surround capillaries with their foot processes and are the primary cells that take up glucose from the blood. Following glycolytic metabolism, astrocytes are known to provide neurons with pyruvate and lactate, which the neurons preferentially oxidize as a mitochondrial metabolic substrate. Thus, with significant injury to astrocytes, neurons would have to utilize glucose directly. This may also be problematic in injured neuronal cells since many recent studies have now found that the key glycolytic enzyme GAPDH is an early target for free radical-mediated damage in neurons and is commonly compromised in acute injury and neurodegenerative diseases (Chuang and Ishitani, 1996).

D. Pyruvate is a Brain Energy Fuel Source With Additional Neuroprotective Properties Another approach for enhancing brain energy levels is to provide a fuel source that could easily cross the blood brain barrier and conveniently enter neuronal metabolic pathways without requiring other cell types. Although high glucose would seem a logical choice, several studies in stroke and head trauma have found that high glucose is detrimental to the injured brain. This may be due to uncoupling of intercellular metabolic coupling or damage to GAPDH as described above. Lactate can serve as a fuel source for neurons but can creat lactic acidosis in patients and also requires conversion to pyruvate inside neurons before it can be utilized. Since the direct provision of pyruvate as a neuronal energy source requires the least number of intervening metabolic steps (FIG. 2) we propose that pyruvate would be an ideal choice as a brain fuel for the injured brain. Pyruvate is indeed preferred by neurons and many other cell types over glucose as a metabolic substrate and is known to result in prolonged neuronal viability in primary cultures. [Selak, 1986 #62] In fact, neurons in serum free medium survive in the complete absence of glucose if pyruvate in present. [Matsumoto, 1994 #56] Addition of pyruvate markedly improves neurophysiological functions in isolated nervous tissue, [Izumi, 1997 #146] and also protects neurons from death induced by hydrogen peroxide (H2O2), [Deshagher, 1997 #50] ischemia, [Matsumoto, 1994 #56] and glutamate [Ruiz, 1998 #60]. These neuroprotective properties of pyruvate may be attributable to its improvement of neuronal energy status. However, pyruvate's ability to scavenge H2O2 and peroxynitrite [Vasquez-Vivar, 1997 #64; Perera, 1997 #241], to improve intercellular calcium buffering [Villalba, 1994 #65; Eimerl, 1995 #72], and to protect mitochondrial metabolism may play a major role as well. As pointed out above, the synthesis of pyruvate by astrocytes, as well as the use of pyruvate by neurons, requires adequate cellular levels of NAD. Since NAD levels can be rapidly diminished by PARP activation, the early activation of PARP may alter compartmentalized metabolic function in the brain and render pyruvate or other fuel sources useless for energy production. This situation, is in a way, analogous to that seen in mitochondrial disorders which affect the brain and also to that seen with Wernike's encephalopathy. In mitochondrial disorders, the mitochondrial gene-derived proteins, which participate in ATP production are deficient. In Wernlike's encephalopathy, a thiamine deficency blocks metabolism of pyruvate through the PDH complex. Nicotinamide treatment of these patients can improve neuronal NAD metabolism and brain energy compartmentation. Indeed nicotinamide can reduce stroke-induced neuronal death in rats, even when given up to two hours after the infarct. [Ayoub, 1999 #48]. Thus, it would seem that providing both nicotinamide and pyruvate to the injured or degenerating brain would significantly improve energy status while at the same time capitalizing on the outstanding ability of these nutrients to scavenge reactive oxygen and nitrogen species. We propose a focused metabolic strategy aimed at preserving neuronal survival using nicotinamide and pyruvate.

E. Creatine Acts to Buffer Brain Energy Pools

The combination of nicotinamide and pyruvate, while facilitating ATP synthesis, may still not adequately provide for improved energy homeostasis in injured or degenerating brain cells. ATP synthesized in brain cells would be rapidly used up were it not for the ability of creatine kinase (CK) to store away energy by coupling the interconversion of creatine to phophocreatine with the conversion of ATP to ADP. This reaction builds up cellular energy stored in the form of phosphocreatine (PC) and also regenerates ADP for new ATP synthesis. Adequate PC stores are very important for large cells such as neurons and skeletal or cardiac muscle cells since the sites of energy production may be far removed from the sites of energy utilization in these cells. Thus PC synthesized in neurons by mitochondria-associated CK can diffuse to sites such as the endoplasmic reticulum, the plasmalemma, or axons where other CK enzymes reverse the reaction to regenerate ATP for local use in functions such as ion transport and axonal transport (FIG. 3). Creatine kinase and its substrates creatine and phosphocreatine thus constitute an intricate cellular energy buffering and transport system connecting sites of energy production (mitochondria) with sites of energy consumption. Indeed, following stress or injury, cellular ATP levels stable initially until the cellular phosphocreatine levels fall below a certain threshold. Both creatine and phosphocreatine can by quantified in the living brain through the use of magnetic resonance spectroscopy (MRS) and such studies have documented altered energy metabolism in injured or degenerating brain regions (Frederico et al, 1997 and 1999) [Tedeschi, 1997 #88 ]. Thus the status of cellular PC levels serves as an important assessment for cellular energy levels. Without adequate intercellular creatine levels, newly synthesized ATP may be rapidly consumed close to the site of its production leaving important neuronal functions unpowered. Although cells can synthesize their own creatine, most cells are not saturated with it. The level of creatine also falls in injured cells although the mechanisms underlying this remain unclear. Creatine, like nicotinamide and pyruvate, easily crosses the blood brain barrier and brain creatine levels can be increased via oral administration (Dechent et al., 1999). Oral administration of creatine, in fact, has been shown to provide effective neuroprotection against MPTP neurotoxicity (Matthews et al, Exp Neurol 157: 142-9, 1999). Oral creatine also provided neuroprotective effects in a transgenic animal model of amyotrophic lateral sclerosis (Klivenyi et al., Nat med 5:347-50, 1999). In this latter study, orally administered creatine produced a dose dependent improvement in motor performance, extended the survival of the transgenic mice, and protected from the loss of both motor neurons and substania nigra neurons. Creatine administration also protected these mice from the increases in biochemical indices of oxidative damage seen in the untreated transgenic mice. This last finding also suggests that maintaining adequate energy buffering may allow cells to repair damage produced by free radicals. Given the distinct roles outlined here for pyruvate, nicotinamide, and creatine in brain energy metabolism it would seem that a combination of these agents may have a synergistic benefit and offer the best opportunity for improving brain energetics.

Rational Therapy Design for Acute and Chronic Brain Injury

In the last two decades many potential neurotoxic mechanism have been implicated in the pathogenesis of both acute and chronic neurodegenerative diseases (FIG. 1). Despite these gains in knowledge, very few clinical advances have been made in treating either acute brain injuries such as trauma and stroke or neurodegenerative diseases. Although many drugs are available for targeting specific neurotoxic events, their clinical toxicity has prevented their benefit from being realized. Also, with so many interrelationships between distinct neurotoxic mechanisms (FIG. 1), it may seem futile to focus on a singular event as the target for therapy. Indeed, many such neurotoxic events may already be peaking by the time a patient comes to clinical attention. A combination pharmacological treatment aimed at several targets may seem logical but this is likely to cause even more toxicity. Applicants believe that by focusing on improving energy metabolism in the injured or degenerating brain, we can achieve much better outcomes than those seen with experimental drugs without the accompanying toxicity. In fact, problems of energy metabolism may be at the heart of pathogenesis in many chronic neurodegenerative diseases. Thus, even if a disease is linked to excessive free radical production, mutations in certain specific proteins, abnormal calcium buffering, or abnormal glutamate transmission, with adequate energy homeostasis cells may be able to compensate for any or all of these deficits. Neurons are the only cells in our body that are meant to last for the duration of our lives. Thus, instead of being looked at as being fragile, neurons are perhaps the hardiest of all cells. Perhaps the late life onset of neurodegenerative diseases actually reflects weakening of the neuronal energy pools, which had been compensating for genetic or other deficiencies all along. We propose that an approach aimed at improving brain energy homeostasis with the combined use of pyruvate as an energy fuel, nicotinamide to boost and replenish the cofactor NAD, and creatine to buffer and efficiently parcel energy utilization, will provide an effective and safe alternative therapy for treating acute and chronic brain diseases.

G. Effective Delivery of Nutrients to the Brain

A specific combination utilizing all three of these agents together has not previously been proposed. Both nicotinamide and creatine taken orally have been demonstrated to raise brain levels of NAD and creatine, respectively. Pyruvate, on the other hand is difficult to deliver to the brain in significant amounts when given orally. Unlike nicotinamide and creatine, pyruvate is quickly consumed by all cells of the body. In fact, most of the pyruvate given orally is consumed by the liver before it can even gain access to the bloodstream. Given the normal role of astrocytes in providing neurons with lactate and pyruvate, a strategy for stimulating astrocytic lactate and pyruvate production would seem to provide the most direct way of delivering pyruvate to neurons (see FIG. 2). While providing high glucose to achieve this goal may seem intuitive, hyperglycemia has been found to actually worsen brain injury resulting from stroke and trauma. Another possible route to enhance astrocytic lactate/pyruvate production is to find an alternative, stable, nontoxic fuel source which astrocytes can convert into lactate/pyruvate. Certain amino acids can achieve this effect (see below). Such a strategy to boost pyruvate synthesis in the body with oral alanine has been used effectively in the past. We have empirically determined that a specific group of aminoacids can markedly stimulate astrocytic pyruvate production (see below).

Toxicology and Clinical Studies, Dosage Selection

Please see the toxicology and dosage selection section in the attached clinical trial proposal which is designed to determine the safety of our nutrient combination in patients with progressive supranuclear palsy, a fatal Parkinson's-like neurodegenerative disease. This trail will take place at Suburban Hospital in Bethesda after funding has been procured. Based on the discussion offered in this clinical trial our patent currently proposes a combination of pyruvate, nicotinamide, and creatine at a dose of 4 g each per day. We will soon have determined the optimal amount of the pyruvate sparing amino acids to utilize in place of pyruvate to achieve better delivery. Our rationale for suggesting the clinical benefits of our nutrient combination stems from our demonstration of the synergistic benefit of the constituents to brain cells, which we will now demonstrate.

Neurons make their own Cr, however the amount of creatine is severly depleted during injury. As with skeletal and heart muscle neuronal Cr stored can easily be increased by oral supplementation of Cr.

Figure 4:
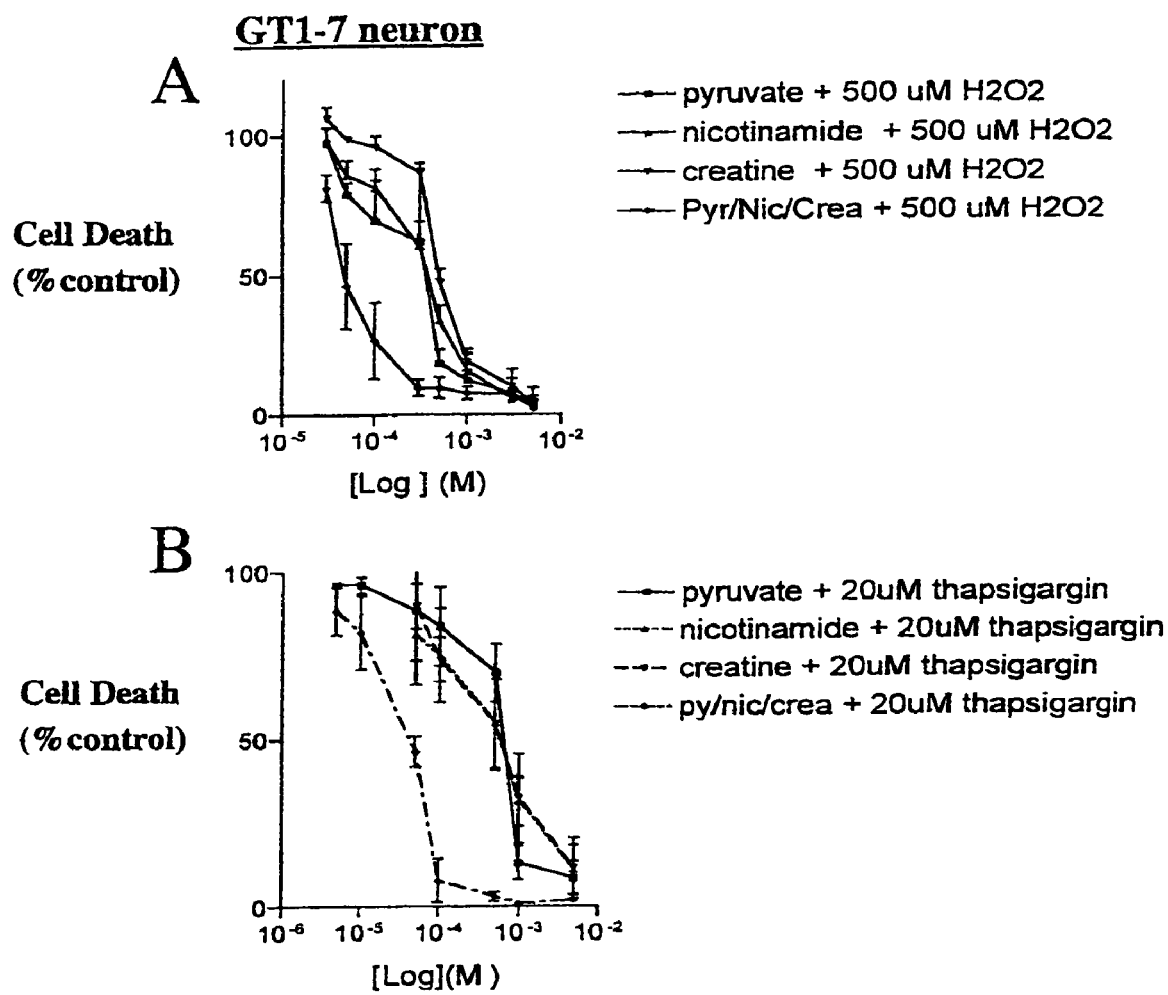
Figure 5:
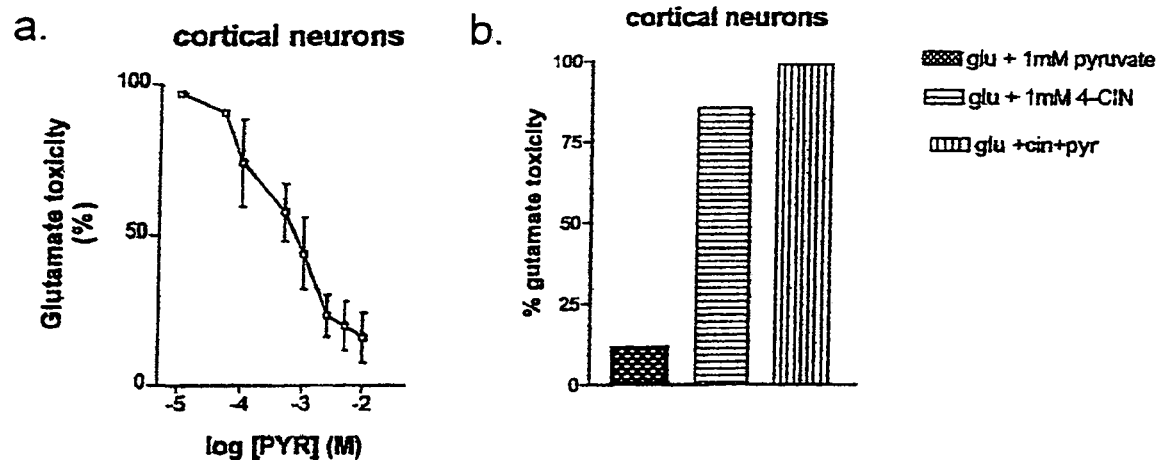

FIG. 4 Shows synergistic neuroprotection by nutrients against free racial and calcium overload toxicity. GT1-7 cell were subjected to treatments and assessed for nutrient neuroprotection as described in the text. All data are means +/− SEM from at least three different experiments. A. H2O2 toxicity, B. Calcium overload toxicity FIG. 5 Shows pyruvate protects rat cerebral cortical neurons from glutamate toxicity. 5a., Rat cortical neurons were treated with a 15 min pulse of 1000 M glutamate in Locke's medium and then further cultured for another 24 hrs in the absence or presence of increasing amounts of pyruvate. Cell death (glutamate toxicity) was measured using the MTT assay. 5b., 4-hydroxycinnamate (4-Cin) has no significant effect on glutamate toxicity alone but prevents the protective effects of pyruvate.

Figure 6:
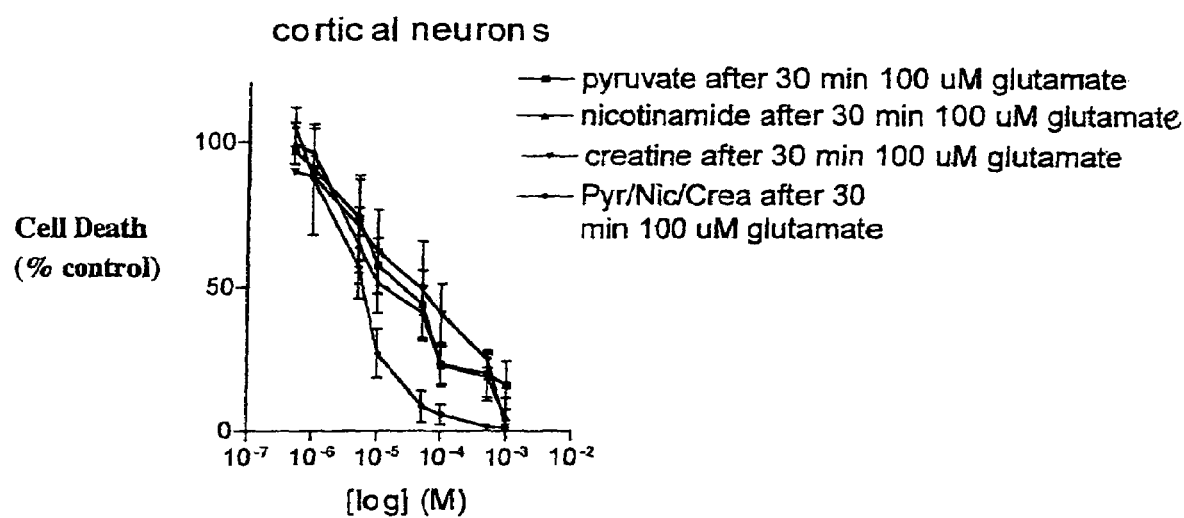

FIG. 6 Shows synergistic neuroprotection by nutrients against glutamate-induced delayed toxicity. Rat cortical neurons were subjected to treatments and assessed for nutrient neuroprotection as described in the text. The glutamate exposure involved treatment wit 100 micromoolar glutamate for 30 min followed by its removal. Nutrients or combinations were present during the exposure and were continued over 24 hrs. All data are means +1-SEM from at least three different experiments.

Figure 7:
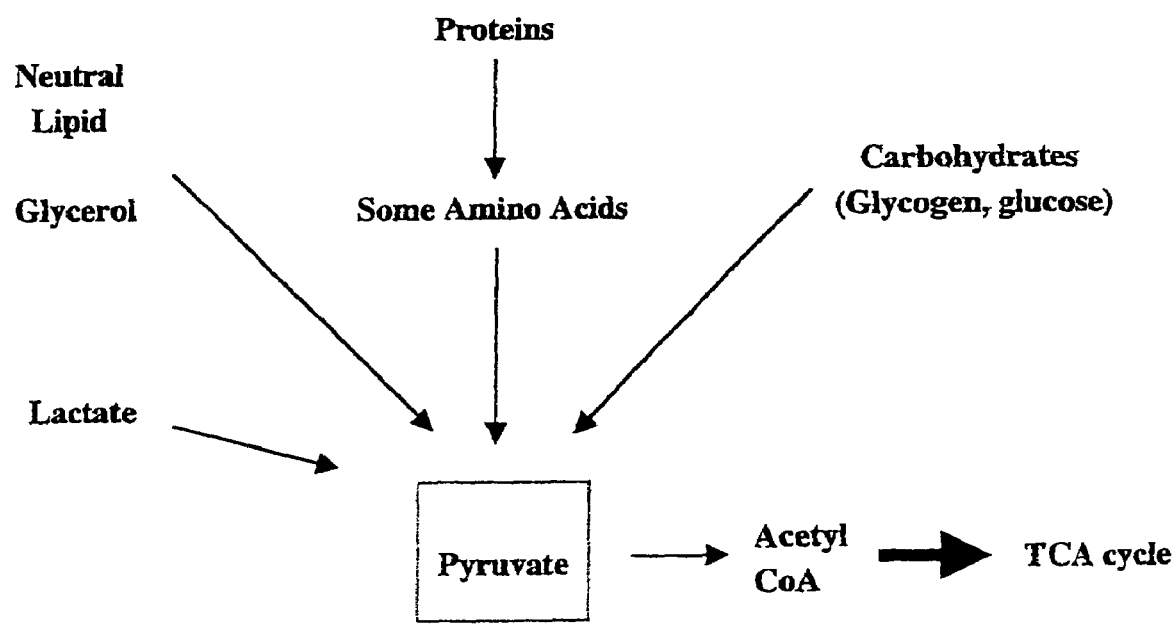

FIG. 7 Shows multiple metabolic routes to pyruvate. While the majority of cellular pyruvate is derived from glucose, there are several other ways that cells can generate pyruvate. Part of our ongoing work is to empirically determine the best orally deliverable substrate, which allows astrocytes to generate pyruvate in the direct vicinity of neurons.

Figure 8:
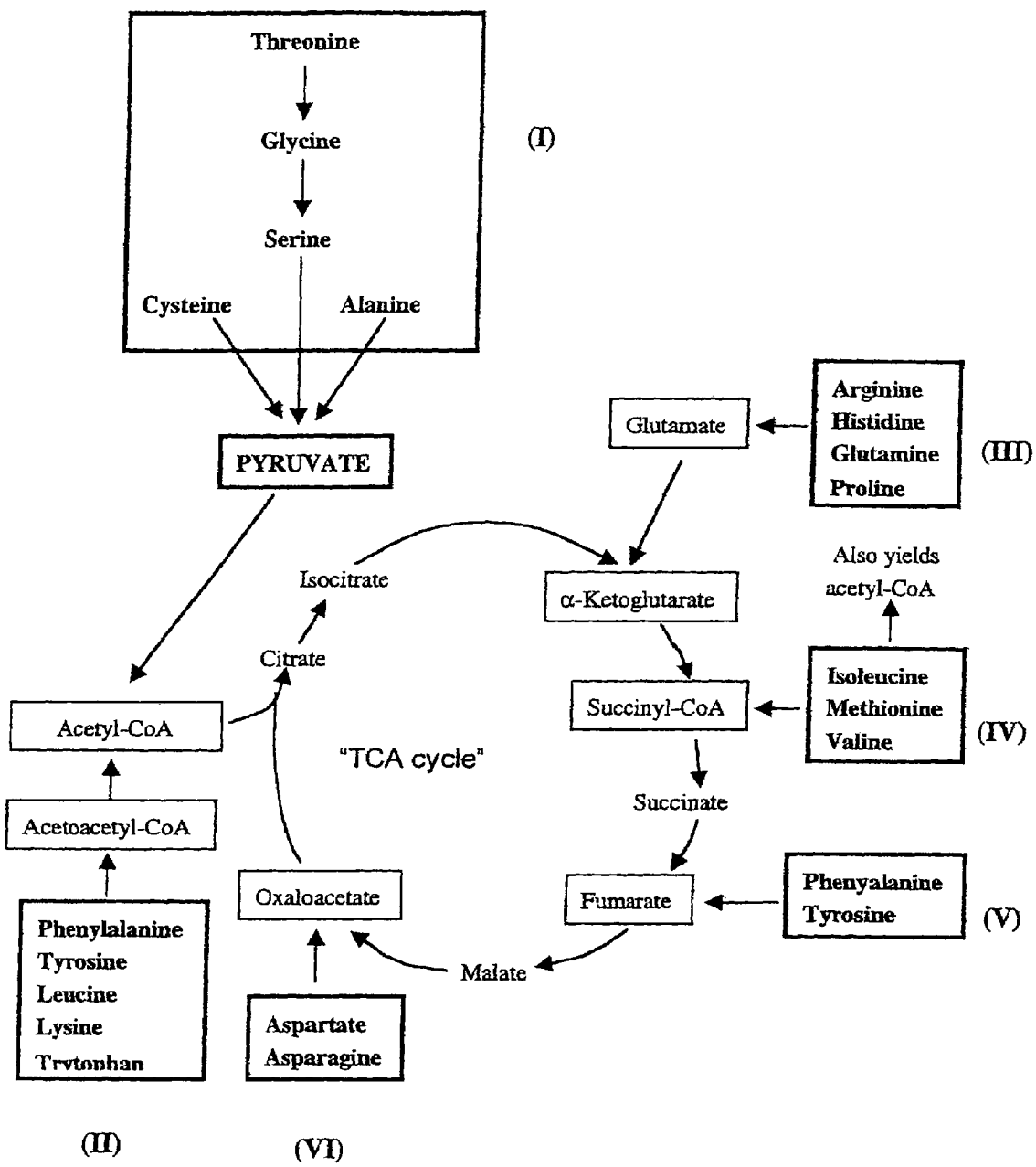

FIG. 8 Shows pathways for amino acids entering energy metabolism. Aminoacids can be utilized by cells to produce energy by entering in to the citric acid cycle, also known as the tricarboxylic acid (TCA) or Krebs cycle. This figure groups amino acids into six (I-VI) groups based on their entry points into these reactions. The six groups depicted here are separately evaluated by us for their cytoprotective and energy enhancing effects in astrocytes.

Figure 9:
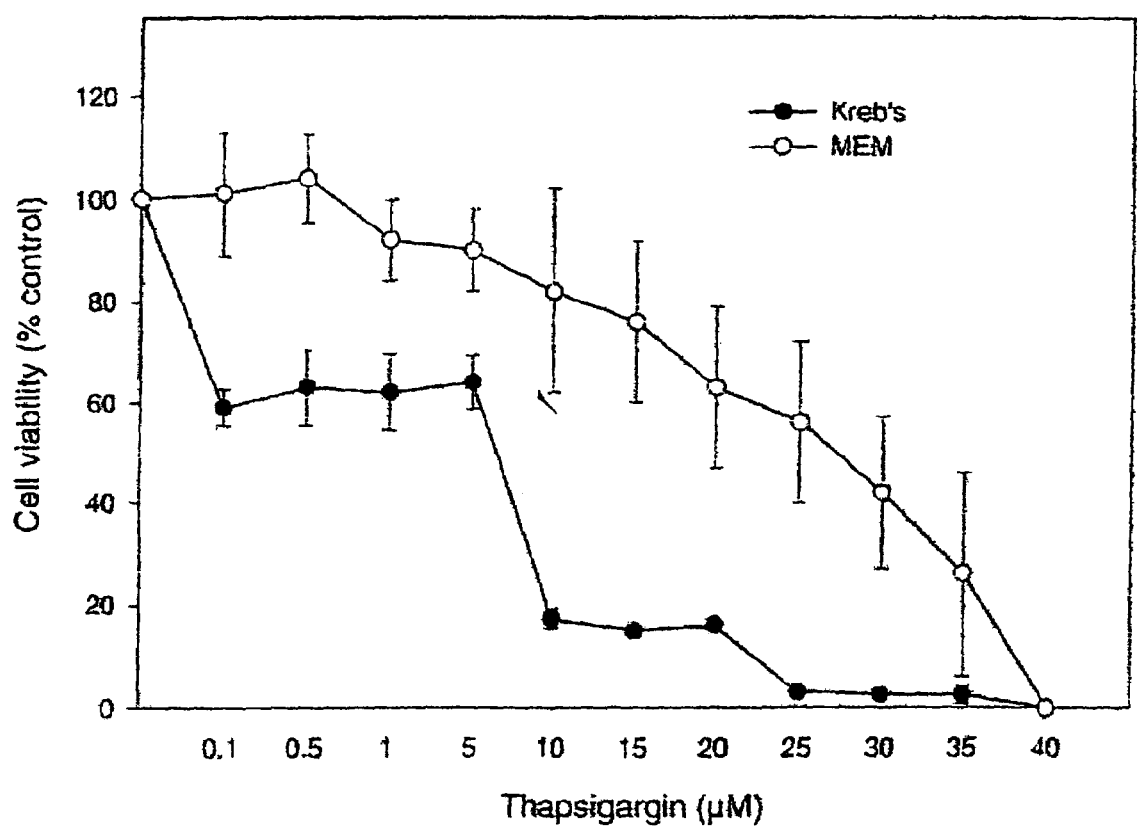

FIG. 9 Shows astrocyte susceptibility to calcium overload is greater in Krebs medium than in MEM. Astrocytes were treated with increasing amounts of the ER calcium pump inhibitor thapsigargin for 24 hrs in either Krebs buffer or MEM. Cell viability was determined using the MTT assay.

Figure 10:
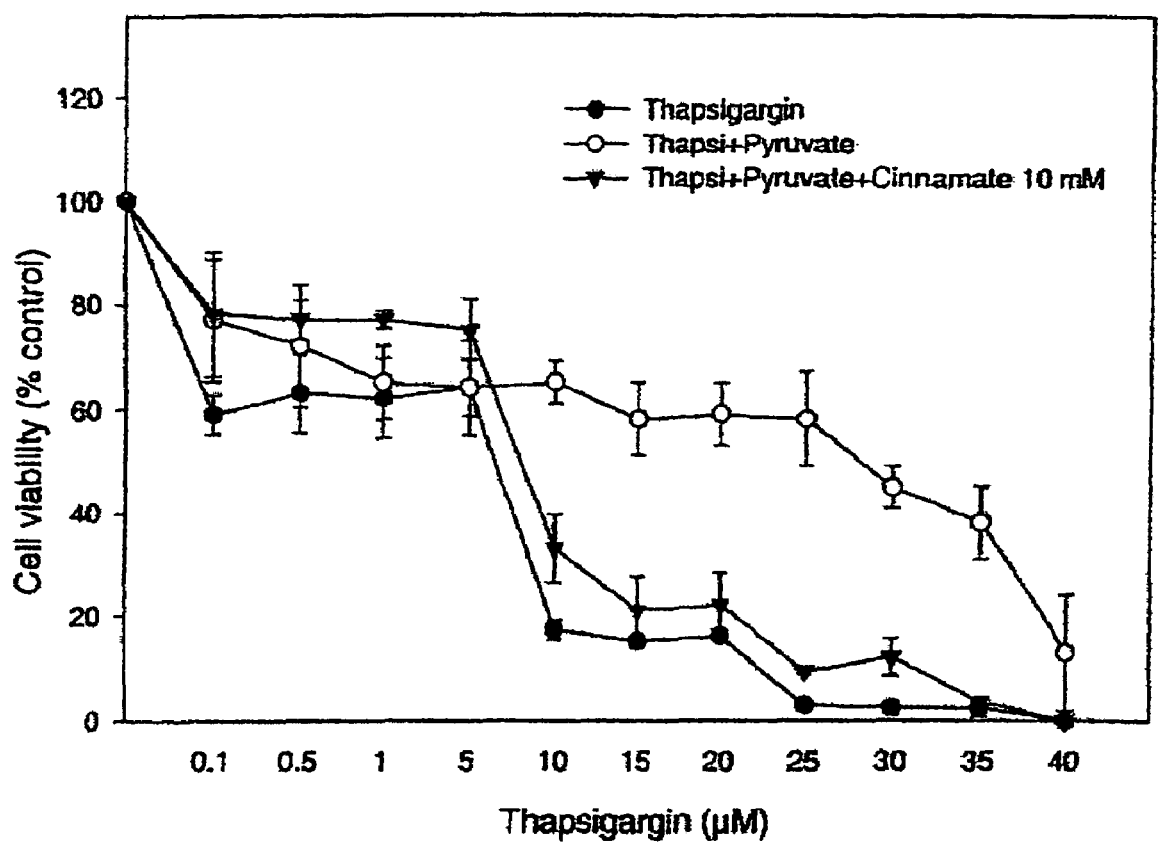
Figure 11:
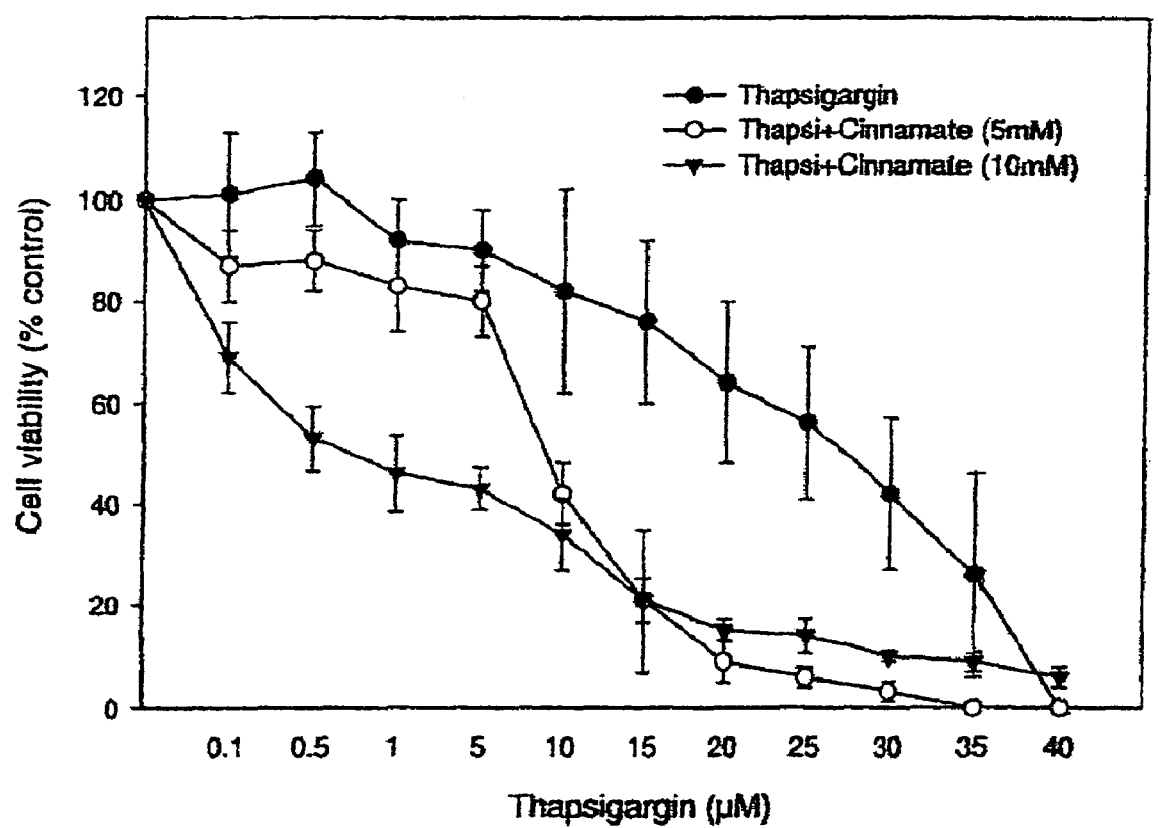

FIG. 10 Shows that the addition of 1 ml V1 pyruvate to Krebs produces a thapsigargin cytotoxic dose response similar to that seen with MEM in FIG. 9 and that this response is prevented by the addition of cinnamate. Conversely, the addition of increasing doses of cinnamate to MEM cultured astrocytes makes the thapsigargin does response profile resemble that seen in Krebs (FIG. 11). This suggests that in MEM, astrocytes make more pyruvate than in Krebs and that the entry of this pyruvate into the mitochondria of astrocytes is required to provide some protection against calcium overload. Presumably this is mediated by pyruvate's main action of enhancing mitochondrial ATP production. The value of using these cytotoxic assays is that accurate measurements of cellular pyruvate directly can be tricky in astrocytes since it is constantly being generated, utilized, turned into lactate and secreted for use by neurons. The really valuable clue offered by these observations is that something in MEM which is not in Krebs is allowing astrocytes to make more pyruvate.

FIG. 11. Cinnamate treatment makes astrocytes cultured in MEM more susceptible to thapsigargin toxicity. These data show that endogenously produced pyruvate in MEM cultured astrocytes provides some protection against calcium overload by entering their mitochondria.

FIG. 10. Exogenous pyruvate provides protection to astrocytes from calcium overload in Krebs Buffer. Addition of 1 mM pyruvate to Krebs buffer provides some cytoprotection and makes the dose response profile of thapsigargin resemble that seen with MEM (compare with FIG. 9). The effect of pyruvate is prevented by cinnamate demonstrating that pyruvate's protective effect requires its entry into mitochondria.

Figure 12:
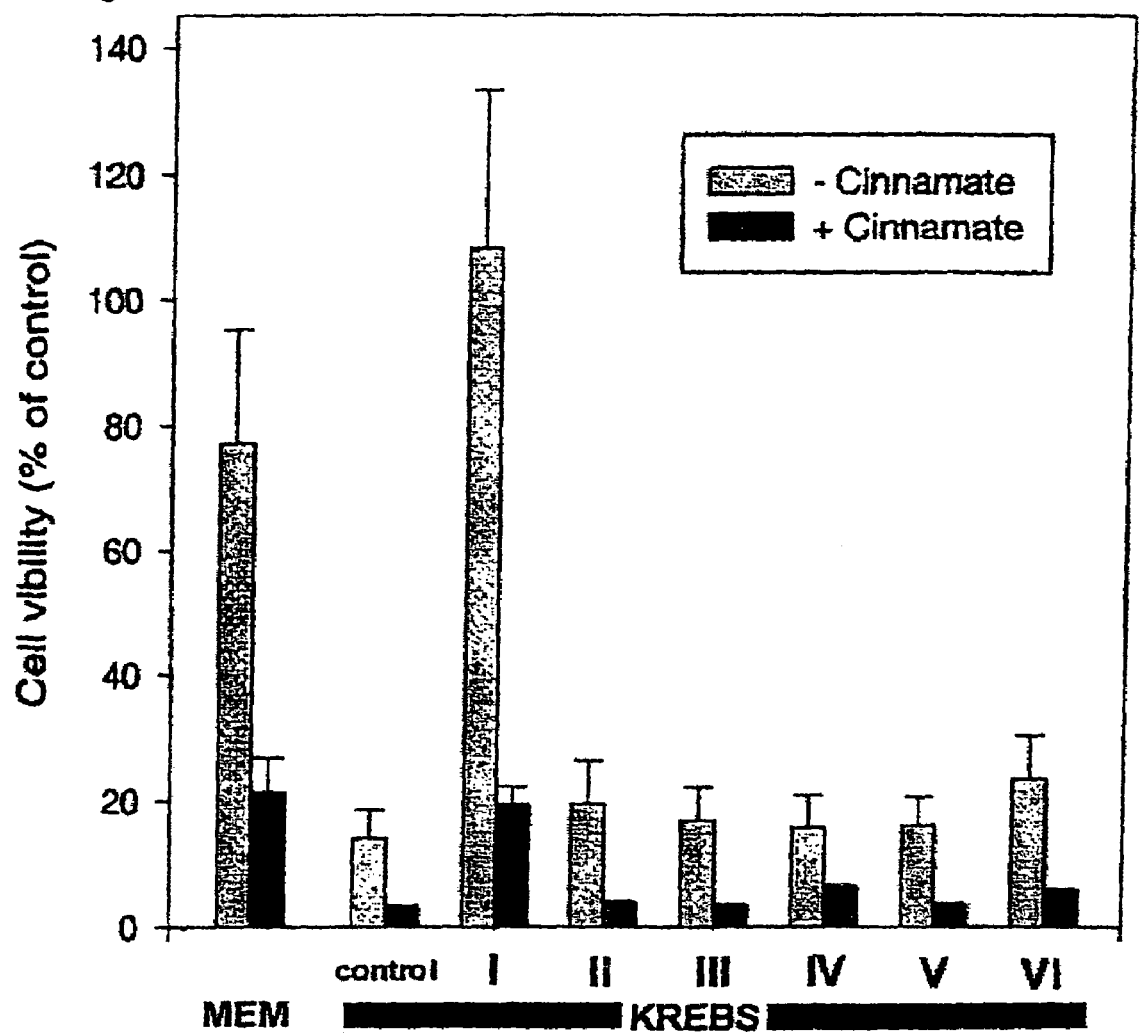

FIG. 12 Shows amino acids provide cinnamate-inhibitable protection for astrocytes from thapsigargin toxicity. For these experiments astrocytes were cultured in either MEM or in Krebs alone or in Krebs with different aminoacid additions grouped as in FIG. 8. Aminoacids were used at 1 mM each. Following 30 min incubation with aminoacids, 15 µM thapsigargin was added to the cultures and the astrocytes cultured for another 24 hours in the presence or absence of 10 mM cinnamate, at which point cell viability was determined using the MTT assay. Cell viability is expressed as percent of that seen with MEM without thapsigargin addition. At the 15 µM thapsigargin dose, about 80% viability is seen in MEM and this is reduced to 20% by the addition of pyruvate. With Krebs, only 20% of the cells are viable after treatment with µM thapsigargin. Note that addition of the aminoacids in group I to the Krebs bufferdes strong protection against thapsigargin toxicity and that this effect is prevented by cinnamate. None of the other aminoacid groups have such an effect.

Figure 13:
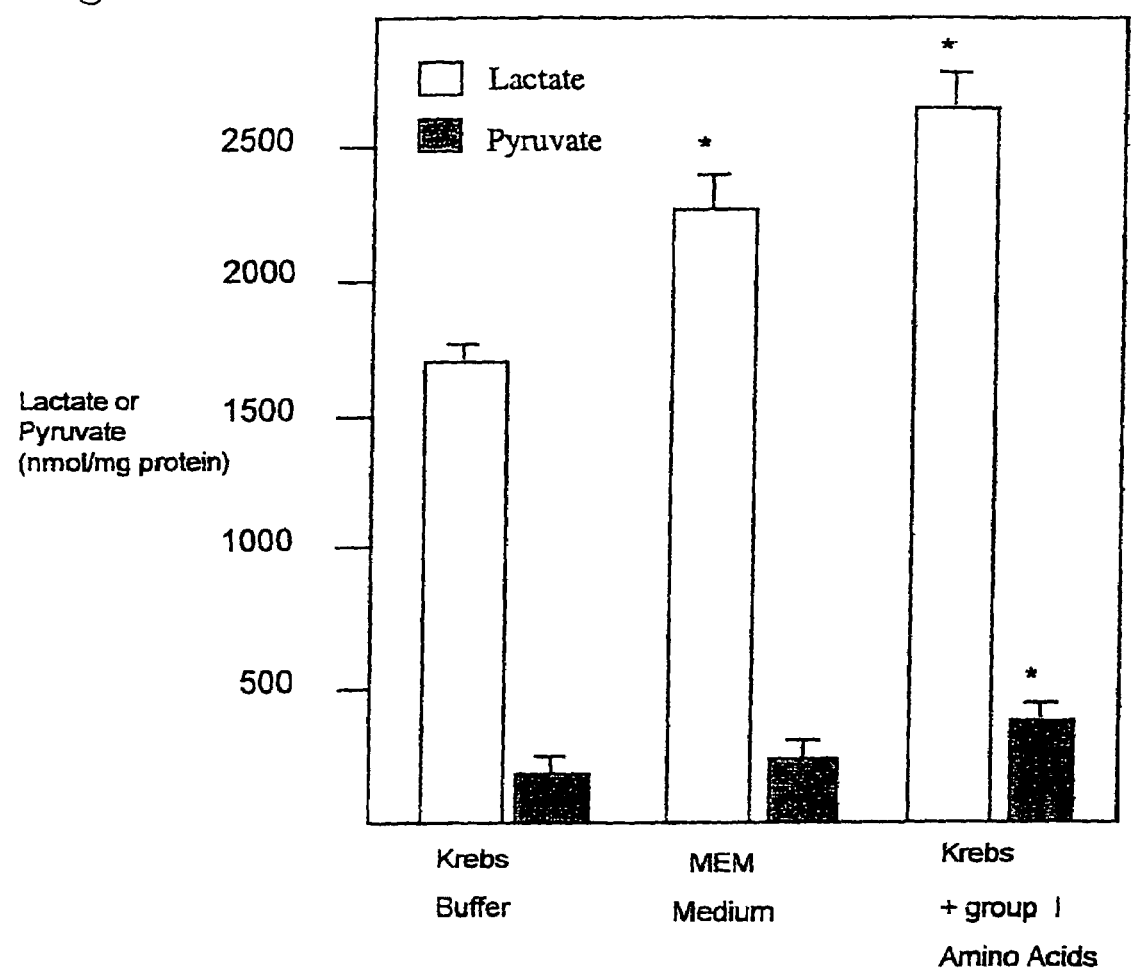

FIG. 13 Shows lactate and pyruvate production by astrocytes. Lactate and pyruvate levels in the media were determined using enzymatic assays. *$P<0.05$ vs. Krebs alone.

EXAMPLES

The following examples are intended to be illustrative of Applicants' invention and do not impose any limitations thereon.

Applicants have discovered a novel, rational, energy metabolism-based treatment for acute and chronic brain afflications using safe, endogenously occurring compounds that can potentially provide neuroprotection against several of the injury mechanisms implicated in neuronal death and degeneration. To further illustrate our invention that simple nutrients can prevent neurotoxicity, we have performed in vitro experiments using cultured neuronal cells subjected to cell killing by reactive oxygen species, calcium overload, and glutamate, the three most commonly sited pathologic events in neurotoxicity. We use the rat hypothalamic neuronal cell line GT1-7 and performed cell killing experiments to determine the dose of hydrogen peroxide just sufficient to kill all cells over a 24 h period of exposure. To study calcium overload toxicity, we treated cells with thapsigargin, an agent that blocks the endoplastic reticulum calcium pump and markedly elevates cytoplasmic calcium levels. To study glutamate neurotoxicity, we utilized primary cultures of rat cortical neurons and used a glutamate pulse model which produces delayed neuronal death in 24 hrs. All studies were performed in Locke's medium prepared in our laboratory to avoid contribution from the vitamins and additives typically found in many commercial media. After determining the toxin treatment dose needed to produce complete toxicity, we then treated the cells dose-dependently with pyruvate, nicotinamide (nicotinamide) and creatine, either alone or in combination along with the LD95 dose of the toxins. We then analyzed the amount of cell death observed after 24 h using a standard cytotoxicty (MTT dye reduction) assay. In the data shown below, we present the % toxicity observed by the indicated treatment protocol after 24 hours on the y-axis as a function of increasing doses of either pyruvate, nicotinamide, or creatine alone or in combination. For the combination experiments, all three agents are added together and the x-axis indicates the concentration of each agent in the combination. As shown in FIG. 4, pyruvate, nicotinamide and creatine are all capable of providing nearly complete dose dependent protection against oxidative stress caused by 500 micromolar H2O2 (FIG. 4A), or calcium overload caused by 20 micromolar thapsigargin (FIG. 4B). The effective concentrations of each agent alone for providing neuroprotection are in the very high micromolar or low millimolar range. When added together, however, these agents produce a more than additive effect with a 10-fold increase in potency. This remarkable synergistic effect has not been previously demonstrated.

Neurons can preferentially use pyruvate as an energy fuel. To see if increasing levels of pyruvate in the medium could demonstrate neuroprotective effects through enhanced energy metabolism, we used a delayed glutamate toxicity model in rat cerebral cortical neurons in the presence of increasing amounts of pyruvate (FIG. 5). To determine whether the protective effects of pyruvate against glutamate toxicity were due to its effect on cell metabolism, we utilized 4-hydroxycinnamate, a compound that blocks the transporter by which pyruvate enters mitochondria. While pyruvate can exert its antioxidant effects in any compartment, its utilization in energy metabolism requires its entry into mitochondria. Pyruvate was found to dose-dependantly protect against glutamate toxicity and this effect required its transport into mitochondria (FIG. 5). These neuroprotective effects of pyruvate have been demonstrated previously. We next determined whether these neuroprotective effects of pyruvate on rat primary neuronal cultures could be potentiated by the addition of creatine and nicotinamide as shown above using GT1-7 cells FIG. 6 demonstrates that when primary cultures of rat cortical neurons are studied for glutamate neurotoxicity, pyruvate, nicotinamide and creatine display even more potent effects in preventing toxicity that those seen in the GT1-7 cell using other injury models. Still, the combined action of these agents shows a remarkable synergistic potentiation with the EC90 values of the combined treatment being more than an order of magnitude greater than with either agent alone (FIG. 6).

TABLES

Table 1 shows the EC50 and EC90 values of these agents alone or in combination for the respective treatment protocols. H2O2 (1a) and Thapsigargin (1b) data are from GT1-7 neurons and Glutamate data is from rat primary neuronal cultures (1c).

TABLE 1

EC50 values for neuroprotecttion by yruvate, nicotinamide, or creatine, alone or in combination. See text for details

|  | EC50 (mM) | EC90 (mM) |
|---|---|---|
| 1a. | | |
| H2O2 | | |
| Pyruvate | 0.35 | 2 |
| Nicotinamide | 0.38 | 2.5 |
| Creatine | 0.49 | 5 |
| Pyr/Nic | 0.98 | 0.41 |
| Pyr/Crea | 0.21 | 0.42 |
| Nic/Crea | 0.31 | 0.44 |
| Pyr/Nic/Crea | 0.047 | 0.3 |

TABLE 1-continued

EC50 values for neuroprotecttion by yruvate, nicotinamide, or creatine, alone or in combination. See text for details

|  | EC50 (mM) | EC90 (mM) |
|---|---|---|
| 1b. | | |
| Thapsigargin | | |
| Pyruvate | 0.58 | 3 |
| Nicotinamide | 0.62 | 5 |
| Creatine | 0.74 | 5 |
| Pyr/Nic/Crea | 0.05 | 0.1 |
| 1c. | | |
| Glutamate | | |
| Pyruvate | 0.05 | 1 |
| Nicotinamide | .055 | 1 |
| Creatine | 0.11 | 3 |
| Pyr/Nic/Crea | 0.008 | 0.05 |

These data demonstrate that the simple nutrients nicotinamide, pyruvate and creatine can synergize to offer effective neuroprotection against several fundamental brain injury mechanisms, which are known to play a major role in many brain diseases. While each of these agents may have additional neuroprotective properties outside of their role in energy metabolism, our major premise is that this combination will provide neuroprotection through enhancement of brain energy levels. To assess this we monitored three different bioenergetic parameters: Whole cell NADH levels, cellular ATP levels and cellular phosphocreatine levels. GT1-7 cells or cross-chopped rat cerebral cortical slices were equilibrated in oxygenated Locke's media for 1 hour. Pyruvate, nicotinamide, or creatine were than added alone or in combination at 1 mM each. Analytes were measured after another hour of incubation.

NADH was measured using its specific fluorescence properties in suspended cells and the effect of each nutrient alone and in combination on GT1-7 neuronal NADH levels is shown in table 2a. Pyruvate would be expected to raise mitochondrial NADH levels through its participation in the Krebs cycle and it indeed appears to account for all of this effect in the combination. ATP and phosphocreatine were measured via a chemiluminescent assay utilizing firefly luciferase. In viable cells, phosphocretine levels most adequately reflect cellular energy supply since cells readily convert any excess ATP into phosphocreatine. In GT1-7 cells each agent had a significant effect on phosphocreatine levels with the combination of all agents having the most pronounced effect (table 2b, *statistically significant vs. Locke's medium alone using Student's one-tailed T-test $P<0.05$).

TABLE 2

Synergistic effect of pyruvate, nicotinamide, and creatine on cellular energy parameters:

| | 2a | |
|---|---|---|
| GT1-7 neurons | | NADH fluorescence |
| Pyruvate (1 mM) | | 134.64 + 9.9* |
| Nicotinamide (1 mM) | | 98.8 + 2.2 |
| Creatine (1 mM) | | 99.3 + 2.3 |
| Pyr/Nic/Crea (1 mM) | | 134.2 + 5* |

TABLE 2-continued

Synergistic effect of pyruvate, nicotinamide, and creatine on cellular energy parameters:

2b

| GT 1-7 neurons | ATP (% control) | CP (% control) | CP/ATP Ratio |
|---|---|---|---|
| Pyruvate (1 mM) | 103.5 + 17.7 | 551.7 + 193.7* | 6 |
| Nicotinamide (1 mM) | 48.6 ± 23.4 | 133.1 + 25 | 4.3 |
| Creatine (1 mM) | 42 + 14.2* | 3314.3 + 920* | 115.2 |
| Pyr/Nic/Crea (1 mM) | 45.5 + 17.1 | 5235.2 + 1304* | 209.7 |

2c

| Cortical slices | ATP % ctr | CP % ctr | CP/ATP ratio | Cortical slices | ATP % ctr | CP % ctr | CP/ATP ratio |
|---|---|---|---|---|---|---|---|
| Pyruvate (1 h) | 77.7 | 233.6 | 3.1 | Pyr/Nic/Crea (1 h) | 49.1 | 356.6 | 7.2 |
| Pyruvate (6 h) | 143.6 | 150.6 | 1 | Pyr/Nic/Crea (6 h) | 353.8 | 344.2 | 1 |

Cross-chopped suspensions of rat cerebral cortex also showed a rise in phophocreatine levels 1 hour after addition of pyruvate alone (left half of table 2c) or the addition of pyruvate in combination with creatine and pyruvate (right half of table 2c). The response with the combination was larger and was maintained after 6 hours of continued incubation. These data support our premise that a synergistic combination of nutrients can indeed enhance cellular energy levels better with either agent alone.

Figure 1:
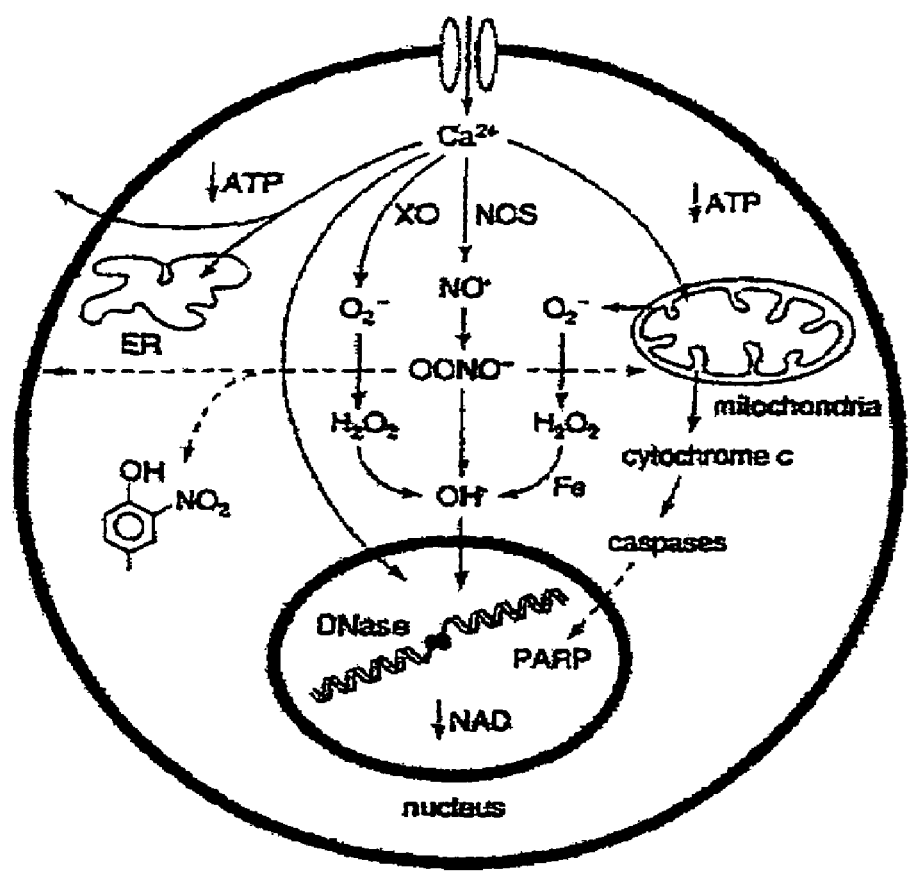
FIG. 1 Shows Cytotoxic interactions between calcium, free radicals, poly (ADP-ribose) polymerase and energy homeostasis. Calcium plays a central role in cytotoxicty and some of its connections with oxygen free radicals, nitric oxide, DNA damage and energy homeostasis are depicted in this figure. Elevated cytoplasmic calcium can strain cellular energy homeostasis in several ways. ATP is required for the removal of calcium from the cytoplasm. Excessive accumulation of calcium by mitochondria impairs oxidative phosphorylation, promotes production of oxygen free radicals such as superoxide ($O_2-$) and hydrogen peroxide ($H_2O_2$) by the electron transport chain, and produces alterations in the permeability of mitochondrial membranes. Altered permeability of the inner membrane inhibits mitochondrial ATP production and promotes necrosis. Selective permeability of the outer membrane, however, appears to be involved in the activation of caspases via release of cytochrome C (Cyt C). Caspases, in turn, cleave key cytoplasmic and nuclear protein substrates to coordinate apoptotic cytotoxicty. Calcium can also directly activate several cellular enzymes that initiate cytotoxic cascades. These include the $Ca^{2+}/Mg^{2+}$ activated endunuclease (DNase) as well as $Ca^{2+}$ sensitive phopholipases and proteases (not shown). Several $Ca^{2+}$ activated enzyme activities are involved in the production of free radicals. $Ca^{2+}$ also activates the calmodulin-regulated enzyme nitric oxide synthase (NOS) which produces large amounts of nitric oxide (NO). Superoxide and nitric oxide can combine to form the much more reactive peroxynitrite anion (OONO). Peroxynitrite can damage many cellular membranes and can lead to oxidation and nitration of proteins containing aromatic amino acids such as tyrosine. DNA damage produced by either the $Ca^{2+}/Mg^{2+}$ activated endunuclease, OONO—, or by hydroxyl radicals results in a robust activation of PARP with subsequent depletion of NAD levels. Since NAD is required for ATP production and since ATP is, in turn, required for NAD synthesis, the net result is a pronounced depletion of the cellular energy pool with resultant necrotic or apoptotic cell death. (Pieper, Verma etal., 1999).
Figure 2:
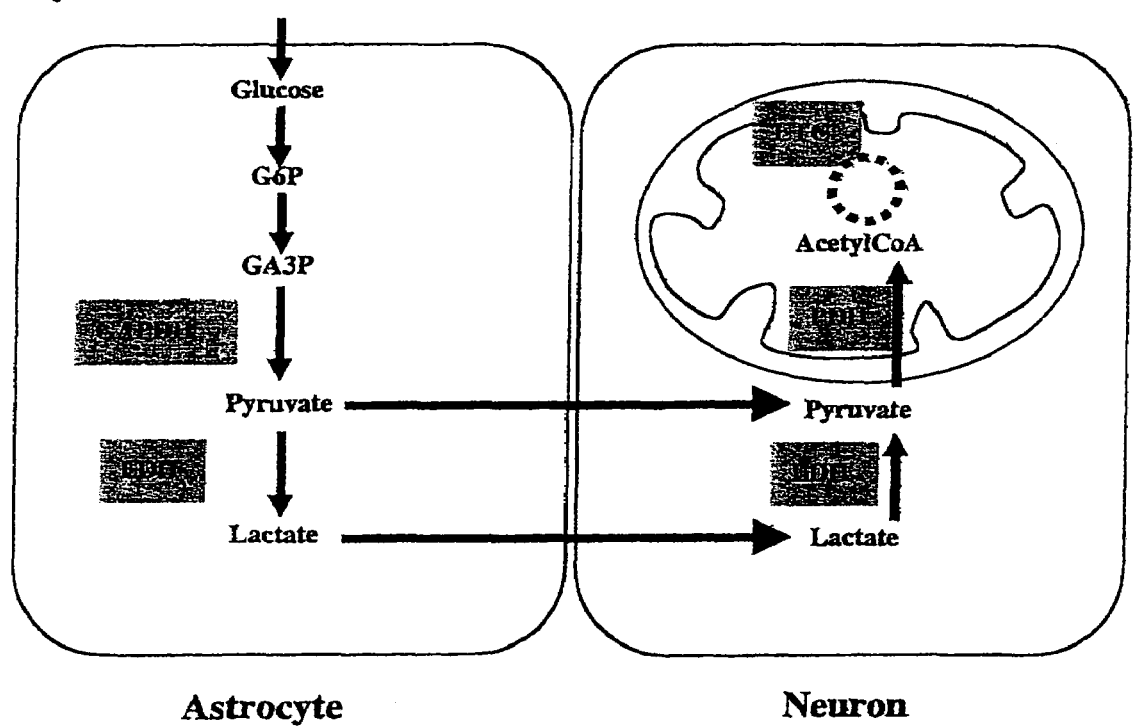
FIG. 2 Shows the critical role of NAD in brain cell metabolic integration. Several key enzymes involved in glycolysis and mitochondrial oxidative metabolism require NAD as a cofactor. These enzymes are depicted in gray boxes in this figure: Glyceraldehyde-3-phosphate dehydrogenase, GAPDH; lactate dehydrogenase, LDH; pyruvate dehydrogenase, PDH; as well as other enzymes in the mitochondrial tricarboxylic acid cycle (shown as a dotted circle) that convert NAD to NADH to feed into site 1 of the mitochondrial electron transport chain. These latter events are all depicted by the gray box labeled ETC. Note that both astrocytes and neurons possess and may display all of these activities when grown separately in culture. The scheme depicted, however, shows the in vivo coupling of metabolic reactions between astrocytes and neurons. Astrocytes are believed to take up glucose from capillaries and then metabolize this to pyruvate and lactate, which they can then transfer to neurons. Neurons, in turn, carry out the bulk of oxidative metabolism via mitochondria. The greater mitochondrial oxidative phosphorylation activity in neurons may also produce more oxygen free radicals in these cells. Note however, that NAD is useless to the cells for energy metabolism in the absence of either glucose, pyruvate, or lactate.
Figure 3:
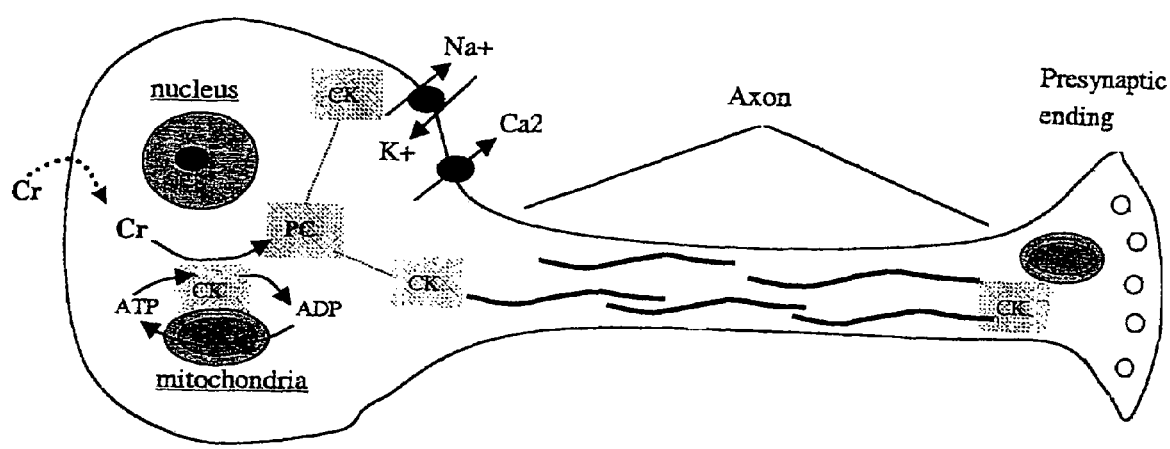
FIG. 3. Crucial role of creatine in buffering and targeting energy delivery in neurons. Mitochondrial creatine kinase (CK) allows the high energy phosphate bond of newly synthesized ATP to be transferred to creatine (Cr), thus generating phosphocreatine (PC), which is much more stable than ATP. PC can diffuse throughout the cell and its high energy phosphate bond can be used to regenerate ATP from ADP only at heavy energy utilization sites where other CK enzymes are strategically positioned. These sites include membranes that engage in heavy duty ion transport, axonal regions involved in transporting material along microtubules to and from presynaptic endings, and the presynaptic endings as well, where energy is required for neurotransmission.

The combination of pyruvate, nicotinamide, and creatine has synergistic benefits for cellular energy metabolism and is also cytoprotective. We are still pursuing further studies to perfect the delivery of this combination to the injured brain. Applicants contemplate the treatment of PSP patients with 4 grams/day each of oral pyruvate, nicotinamide, and creatine for two months. Among the parameters considered to be important to measure are cerebrospinal fluid pyruvate and lactate levels pre- and post-treatment. Nevertheless, we are also pusuing alternative ways of increasing pyruvate availability to neurons. As an alternative approach for delivering pyruvate to neurons, we have begun to determine whether astrocytes can be made to produce pyruvate (or lactate which neurons can then convert to pyruvate) from amino acids. While there are several metabolic routes to pyruvate which utilize different metabolic substrates (FIG. 7), we believe that aminoacids (FIG. 8) represent the safest means to accomplish this based on previous studies demonstrating deleterious effects of excessive carbohydrates and lactate administration to the injured brain. Aminoacids are also easy taken orally, have a long circulating half-life, and can even be made into sustained-release formulations. Indeed, an alanine loading test which has been clinically used to raise whole body pyruvate levels, utilizes 0.1-0.2 g/Kg oral loading doses safely. This would represent 7 to 14 g of oral alanine for a 70 Kg person that have been taken safely in a single dose. Neurons are known to have higher levels of NAD and creatine than astrocyte, but pyruvate is primarily produce by astrocytes in the intact brain (see FIG. 2) and may even have cytoprotective effects for astrocytes as well. When astrocytes are grown alone in culture, they produce pyruvate and utilize it in large part for their own metabolism. Since we had shown that pyruvate protects neurons from calcium overload induced by thapsigargin toxicity, we first determined whether endogenously produced or exogenously supplied pyruvate could protect astrocytes from calcium overload induced by thapsigargin as shown previously for GT1-7 neurons. To determine this we cultured rat cerebral cortical astrocytes in either Minimum Essential media (MEM) or Krebs buffer. MEM and Krebs buffer do not contain added pyruvate as do some other cell culture media. MEM does however have aminoacids which not contained in Krebs. As shown in FIG. 9, rat brain astrocytes are dose-dependantly killed by 24 h exposure to thapsigargin in both media. The cytotoxic potency of thapsigargin is much greater however in Krebs than in MEM.

To determine whether this differential sensitivity of astrocytes to thapsigargin reflected the protective effect of differentially generated endogenous pyruvate in the two media, we again utilized additions of pyruvate and 4-hydroxycinnamate, which blocks the entry of pyruvate into mitochondria.

These data suggest that astrocytes in culture generate more pyruvate when cultured in MEM than in Krebs and that this pyruvate's contribution to energy metabolism iva entry into mitochondria provides protection for astrocytes against calcium overload. MEM does not contain added pyruvate. In fact, Krebs has much more glucose than MEM, but does contain the amino acids found in MEM. We therefore hypothesized that astrocytes can produce pyruvate from aminoacids as can other cells of the body. To determine if this were the case, we first empirically determined which of the different groups of aminoacids shown in FIG. 8 could provide a protective effect against thapsigargin for astrocytes cultured in Krebs. To determine that his protective effect was mediated via pyruvate generation, we also utilized the cinnamate sensitivity of any such protective effect. As shown in FIG. 12, the most effective group of aminoacids was Group I, the aminoacids that can be metabolized directly into pyruvate.

Finally, to see whether we could directly determine stimulation of astrocyte pyruvate or lactate production by the group I aminoacids we cultured astrocytes in MEM, Krebs, or Krebs plus imM each of the group I aminoacids for 24 hrs and then determined the amount of pyruvate or lactate in the culture media. We had previously determined that nearly all the measurable pyruvate or lactate in these cells readily leaves the cell and accumulates in the medium.

These data suggest that we can empirically determine novel ways of stimulating astrocyte pyruvate and lactate production and thus put into practice the metabolic principles we have outlined. Altogether, our data support our hypothesis that targeting neuronal energy enhancement using our approach provides a sound, rational, and powerful new direction in neuroprotection. We believe that our synergistic effects will allow us to see clinical benefits that may be missed with monotherapy using these agents. Furthermore, the low cost, immediate availability and clinical safety of the agents we are employing makes our approach even more attractive.

DETAILED DESCRIPTION OF THE INVENTION

NOVEL FEATURES: Biological activity has been discovered for a pharmaceutical composition whose dominant function is to be either (1) reactive with antigens (to neutralize viruses or coat bacteria) which may be released, separate and in sequence with, a salt of an alpha-keto carboxylic acid wherein the salt enhances the phosphorylation potential and reduces hydrogen load within the cell thereby preventing the deterioration or promoting the restoration and preservation of normal cell functions or (2) enhance the phosphorylation potential and reduce the hydrogen load within the cell thereby preserving or improving cell functions. Additionally, biological activity has been discovered for a pharmaceutical composition whose dominant function is to decrease the activity of the (hepatic) HMG CoA reductase and hence cholesterol biosynthesis. The resulting decrease in intercellular cholesterol will stimulate the production of LDL receptors and hence accelerate cellular uptake of plasma cholesterol thereby reducing and/or eliminating hypercholesteremia. More precisely, applicant has discovered a pharmaceutical composition, method of making and use thereof a bioactive substance alone, and in combination with a salt of an alpha-keto carboxylic acid, or said salt alone with the following attendant itemized features.

1. A method for inhibiting the proliferation of rapidly replicating abnormal cells caused by pathogenic substances and enhancing the phosphorylation potential within the normal cells of a mammal or a biological system in order to prevent an/or ameliorate the deterioration or promote the restoration and preservation of normal cell functions comprising, administering concurrently together or by separate and sequential dosage, to the cells of a mammal in need thereof or delivering to a biological system a pharmaceutical composition comprising (1) at least one neutralizing antibody, (2) a salt of an alpha-keto carboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted naphthyl wherein the ring is mono-, di-, or trisubstitued and the substitutents are alkyl of 1 to 4 carbon atoms, halo, alkoxy of 1 to 4 carbon atoms, phenoxy, trihalomethyl, dimethylamino, diethylamino, and M is a cation, alone or in combination with nicatinamide, creatine and/or an aminoacid combination thereof, wherein said antibody is first administered until the neutralization of the pathogenic substance has been completed before a separate and sequential dosaging regimen is employed.

2. The method in accordance with Feature 1 wherein said cation is an alkali or alkaline earth metal.

3. The method in accordance with Feature 2 wherein the alkali metal is sodium.

4. The method in accordance with Feature 3 wherein R is an alkyl group containing 1 to 12 carbon atoms.

5. The method in accordance with Feature 4 wherein the alkyl group is methyl.

6. A method in accordance with Feature 1 wherein the composition is a parenteral fluid.

7. A method in accordance with Feature 1 wherein the composition is an incubation medium.

8. A method according to Feature 6 wherein the parenteral fluid is selected from the group comprising total parenteral nutritional fluids; kidney and peritoneal dialyses fluids; volume and plasma expanding fluids; pyruvate/acetate near-isotonic solutions; lactate/acetate-free pyruvate isotonic solutions; normal saline solutions; hemoglobin-substitute containing solutions; vitamin supplement product; and cardioplegic solutions.

9. A method according to Feature 6 wherein the amount of said salt is effective in reducing and/or ameliorating intercellular acidosis.

10. A method according to Feature 6 wherein the amount of said salt is effective in neutralizing hydrogen peroxide through hydrogen peroxide-alpha-ketocarboxylate interaction to inhibit the formations of toxic-free radicals.

11. A method in accordance with Feature 1 wherein the composition is a rehydration fluid, which may be augmented with electrolyte balances.

12. A method in accordance with Feature 11 wherein the rehydration fluid contains electrolyte balances.

13. A method in accordance with Feature 13 wherein the composition is a topical composition.

14. A method according to Feature 13 wherein the topical composition is selected from the group comprising medicinal soaps; medicinal shampoos; sunscreens; medicinal ointments; vitamin capsules; dentrifice; mouthwash; douche solutions; and medicinal baths.

15. A method in accordance with Feature 1 wherein the composition is augmented with an antibiotic or antiphlogistic.

16. A method in accordance with Feature 15 wherein the composition is contacted by intramuscular, intravenous, intraperitoneal, injection, parenterally, transfusion or orally.

17. A composition for inhibiting the proliferation of rapidly proliferating abnormal mammalian cells and enhancing the phosphorylation potential within the cells of a mammal or a biological system in order to prevent and/or ameliorate the deterioration or promote the restoration and preservation of normal cell functions, by administering concurrently together or by separate and sequential dosages of ingredients, comprising (1) at least one antibody and (2) a therapeutically effective amount of a salt of an alpha-ketocarboxylic acid having the formula R-C(0)(CO)OM wherein R is a alkyl of 1 to 12 carbon atoms; substituted alkyl of 1 to 12 carbon atoms; cyloalkyl of 3 to 10 carbon atoms; alkenyl of 2 to 6 carbon atoms; alkynyl of 3 to 6 carbon atoms; benzyl; substituted benzyl (wherein the substituent is methyl, phenyl on the alpha carbon atoms or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstitued and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

18. An augmented composition for inhibiting the proliferation of rapidly replication abnormal mammalian cells and enhancing the phosphorylation potential within the normal cells of a mammal or a biological system in order to present and/or ameliorate the deterioration or promote the restoration and preservation of normal cell functions which comprises:

A. A therapeutic cell normalizing composition which comprises: (1) At least one antibody and (2) a therapeutically effective amount of salt of an alpha-keto carboxylic acid having the formula R-C(0)(CO)OM wherein R is alkyl of 1 to 12 carbon atoms; substituted alkyl of 1 to 12 carbon atoms; cyloalkyl of 3 to 10 carbon atoms; alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl 6 halo, dihalo; or ethoxy on the phenyl ring); adamantyl; phenyl; napthyl; substituted phenyl or substituted napthyl (wherein the ring is mono-, di, or trisubstitued and the subsntuents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid; and B. a medicament useful for treating injured cells.

19. The augmented composition according to Feature 18 wherein the medicament is selected from the group consisting of antibacterial agents, antiviral agents, antifungal agents, antimicrobial agents, antiprotozoan agents, antipollen agents, antivenom agents, antiparasitic agents, antiyeast agents, mmunostimulating agents, antikeratolytic agents, antiinflammatory agents, acne treating agents, sunscreen agents, dermatological agents, antihistamine agents, bioadhesive agents, respiratory bursting inhibitors, inhibitors of prostaglandin synthesis, antiseptic agents, anesthetic agents, cell nutrient media, burn relief medications, sun burn medications, insect bite and sting medications, wound cleaners, wound dressings scar reducing agents, glucose (dextrose), creatine, aminoacids, medicinal soaps, medicinal shampoos, medicinal ointment, vitamin capsules, dentrifice agents, mouthwashing agents, douche solution, anti-cancer agents, medicinal baths, antibiotics, antitumor agents, antipyrectics analgesics, antitussives, expectorants, sedatives, muscle relaxants, antiulcer agents, antidepressants, antiallergic drugs, cardiotonics, vasodilators, factors, narcotic antagonists, analgesics, spermicidal compounds, gastrointestinal therapeutic agents, protease inhibitors, and insulins.

20. A parenteral fluid useful for inhibiting the growth of rapidly proliferating abnormal mammalian cells and, enhancing the phosphorylation potential within the cells of a mammal in order to prevent the deterioration or promote the restoration and preservation of normal call functions, by administering concurrently or by separate and sequential dosages of ingredients, comprising (1) at least one antibody and (2) a therapeutically-effective amount of a salt of an alpha-keto carboxylic acid having the formula R-C(0)(CO)OM wherein R is alkyl of 1 to 12 carbon atoms; substituted alkyl of 1 to 12 carbon atoms, cyloalky of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantly; phenyl; naphthyl; substituted phenyl or substituted naphthyl (wherein the ring is mono-, di-, or trisubstitued and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

21. A composition according to Feature 20 wherein the parenteral fluid is selected from the group comprising total parenteral nutritional fluids; kidney and peritoneal dialyses fluids; volume and plasma expanding fluids; pyruvate/acetate near-isotonic solutions; lactate/actuate-free pyruvate isotonic solutions; normal saline solutions; hemoglobin-substitute containing solutions; vitamin supplement product; and cardioplegic solutions.

22. A rehydration fluids, which may be augmented with electrolyte balances, useful for inhibiting the proliferation of rapidly proliferating abnormal mammalian cells and, enhancing the phosphorylation potential within the cells of a mammal in order to prevent the deterioration or promote the restoration and preservation of normal cell functions, by administering concurrently or by separate and sequential dosages of ingredients, comprising a (1) at least one antibody and (2) therapeutically-effective amount of a salt of an alpha-ketocarboxylic acid having the formula RC(0)(CO)OM wherein R is alkyl of 1 to 12 carbon atoms; substituted alkyl of 1 to 12 carbon atoms, cyloalkyl of 3 to 10 carbon atoms, alkynyl of 2 to 6 carbon atoms; allkynyl of 3 to 6 atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstiued and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

23. A composition according to Feature 22 wherein the rehydration fluid contains electrolyte balances.

24. A medicinal composition useful for enhancing the phosphorylation potential within the cells of a mammal in order to prevent the deterioration or promote the restoration and preservation of normal cell functions, by administering concurrently or by separate and sequential dosages of ingredients, comprising (1) at least one antibody and (2) a therapeutically effective amount of thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted naphthyl (wherein the ring in mono-, di-, or trisubstitued and the substitutents are alkyl of 1 to 4 carbons atoms, halo, alkoxy of 1 to 4 carbon atoms, phenoxy, trihalomethyl, dimethylamino, diethylamino, and M is a cation alone or in combination with nicatinamide, creatine and/or an aminoacid.

25. A composition according to Feature 24 is selected from the group comprising medicinal soaps; medicinal shampoos; sunscreens; medicinal ointments; vitamin capsules; dentrifice; mouthwash; douche solutions; and medicinal baths.

26. An antibiotic or antiphylogistic composition useful for enhancing the phosphorylation potential within the cells of a mammal in order to prevent the deterioration or promote the restoration and preservation of normal cell functions, by administering concurrently or by separate and sequential dosages of ingredients, comprising (1) at least one antibody and (2) a therapeutically effective amount of a salt of an alpha-ketocarboxylic acid having the formula RC(0)(CO)OM wherein R is alkyl of 1 to 12 carbon atoms; substituted alkyl of 1 to 12 carbon atoms, cyloalkyl of 3 to 10 carbon atoms, within the alkylene chain, halogen amino, alhylamino of 1 to 4 carbon atoms, dialkylamino of 1 to 4 carbon atoms in each alkyl, alkenyl of 2 to 6 carbon atoms; aikynyl of to 6 carbon atoms; benzyl; substituted benzyl (wherein the substituent is methyl, phenyl of the alpha carbon atom or the substituent is methyl, dimethyl, halo, dihalo, or ethoxy of the phenyl ring); adamantyl; phenyl; naphthyl; substituted phenyl or substituted naphthyl (wherein the ring is mono-, di, or trisubstituted and the substitutents are alkyl of 1 to 4 carbons atoms, halo, alkoxy of 1 to 4 carbon atoms, phenoxy, trihalomethyl, dimethylamino, diethylamino, and M is a cation alone or in combination with nicatinamide, creatine and/or an aminoacid.

27. An aerosolized pharmaceutical composition for enhancing the phosphorylation potential within the cells of a mammal in order to prevent the deterioration or promote the restoration of normal cell functions, by administering concurrently or by separate and sequential dosages of ingredients, comprising (1) at least one antibody and (2) a therapeutically effective amount of a slat of an alpha-keto carboxylic acid R-C(0)(CO)OM wherein R is alkyl of 1 to 12 carbon atoms; substituted alkyl of 1 to 12 carbon atoms; cyloalkyl of 3 to 10 carbon atoms, (carboxyalkylene of 1 to 20 carbon atoms within the alkylene chain, halogen amino, alkylamino of 1 to 4 carbon atoms, dialkylamino of 1 to 4 carbon atoms in each alkyl group or phenyl); alkenyl of 2 to 6 carbon atoms; alkynyl of 3 to 6 atoms; benzyl; substituted benzyl (wherein the substituent is methyl, phenyl on the alpha carbonation or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstitued and the substitutents are alkyl or 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or and aminoacid, and (3) a bronchodilating agent.

28. A perfusion fluid for enhancing the phosphorylation potential within the cells of mammal in order to prevent the deterioration or promote the restoration and preservation of normal cell functions, by administering concurrently or by separate and sequential dosages of ingredients, comprising (1) at least one antibody and (2) therapeutically effective amount of a salt of an alpha keto-carboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstitued and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

29. A food product for enhancing the phosphorylation potential within the cells of a mammal in order to present the deterioration or promote the restoration and preservation of normal cell functions thereby enhancing physical endurance or refreshment comprising a pharmaceutical composition having as active ingredients, released concurrently together or separately in sequence, thereof (1) at least one antibody and (2) a therapeutically effective amount of a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkenyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstitued and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

30. The food product in accordance with Feature 29 wherein said food product is in liquid form.

31. A vitamin supplement product for enhancing the phosphorylation potential within the cells of a mammal in order to prevent the deterioration or promote the restoration and preservation of normal cell functions hereby enhancing physical endurance or refreshment comprising, releasing concurrently or by separate and sequential dosages of ingredients therefrom, (1) antibody and (2) a therapeutically effective amount of a salt of an alpha-keto carboxylic acid having the formula R-C(0)(CO)OM wherein R is alkyl of 1 to 12 carbon atoms; substituted alkyl of 1 to 12 carbon atoms, cyloalkyl of 3 to 10 carton atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo dihalo, or ethoxy on the phenyl ring); adamantyl; phenyl; naphthyl; substituted phenyl or substituted naphthyl (wherein the ring is mono-, di-, or trisubstitued and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

32. A neutralizing antibody prepared by the process comprising the steps of:
   a. Exposing a patient to a pathogen such that said patient produces, in its blood or milk, neutralizing antibodies to said pathogen;
   b. Separating the serum from the blood or the fat from the milk;
   c. Collecting the serum from the blood or the nonfat component of the milk;
   d. Treating the serum or non-fat component of the milk, which contains neutralizing antibodies, with a supersaturated solution of ammonium sulfate at a rate of about 30 drops per minute (0.05 cc per drop) until precipitation is complete;
   e. Centrifuging the product of step d., thereby producing a (NH4)2 SO4+neutralizing antibody complex and a supernatant layer;
   f. Removing the supernatant layer from the (NH4)2 SO4 neutralizing antibody precipitate;
   g. Adding super-saturated ammonium sulfate to the ammonium sulfate-neutralizing antibody complex to form a solution;
   h. Pouring the solution of step g. into a dialysis bag having a plurality of holes with per unit of less than about 10,000;
   i. Placing the dialysis bag of step h. in a magnetic stirring device and add dialysate buffer,
   j. Stirring the dialysis bag and dialysis bag and dialysate buffer for about 2 hours and replacing the discolored dialysate with a fresh supply of clear dialysate each stirring period;
   k. Adding silver nitrate to a sample of dialysate solution from step i. to determine if the neutralizing antibody is free of ammonium sulfate as confirmed by the absence of silver sulfate formation (precipitate);
   l. Repeating step k. for about 24 hours until the dialysate remains clear in color,
   m. Separating the dialysate solution from the dialysis bag containing the ammonium sulfate-free neutralizing antibody; and
   n. Collecting the neutralizing antibody.

33. A neutralizing antibody of Feature 32 wherein the neutralizing antibodies in step c. are polyclonal antibodies.

34. A neutralizing antibody prepared in accordance with Feature 33 wherein the pathogen is selected from the group consisting of bacteria, fungi, protozoa, pollen, venom, parasites, yeasts, viruses, and combinations thereof.

35. A neutralizing antibody prepared in accordance with Feature 34 wherein the pathogen is a virus.

36. A neutralizing antibody prepared in accordance with Feature 35 wherein the virus is a retrovirus.

37. A neutralizing antibody prepared in accordance with Feature 36 wherein the retrovirus is human immunodeficiency virus.

38. A neutralizing antibody prepared in accordance with Feature 37 wherein the human immunodeficiency virus is HIV-1.

39. A method of producing antibodies for the treatment of infection in a patient by a pathogen, comprising the steps of
  a. Exposing a patient to a pathogen such that said patient produces, in its blood or milk, neutralizing antibodies to said pathogen
  b. Separating the serum from the blood or the fat from the milk;
  c. Collecting the serum from the blood or nonfat component of the milk, which contains neutralizing antibodies, with a super-saturated solution of ammonium sulfate at a rate of 30 drops per minute (0.05 cc per drop) until precipitation is complete;
  d. Treating the serum or nonfat component of the milk, which contains neutralizing antibodies, with a super-saturated solution of ammonium sulfate at a rate of about 30 drops per minute (0.05 cc per drop) until precipitation is complete;
  e. Centrifuging the product of step d., thereby producing a (NH4)2 SO4* neutralizing antibody complex and a supernatant layer;
  f. Removing the supernatant layer from the (NH4)2 SO4* Neutralizing antibody precipitate;
  g. Adding super-saturated ammonium sulfate to the ammonium sulfate neutralizing antibody complex to form a solution;
  h. Pouring the solution of step g. into a dialysis bag having a plurality of holes with a pore size which permit the emptying out of substances having a molecular weight per unit of less than about 10,000;
  i. Placing the dialysis bag of step h. in a magnetic stirring device add dialysate buffer;
  j. Stirring the dialysis bag and dialysate buffer for a period of about 2 hours and replacing the discolored dialysate with a fresh supply of clear dialysate at the end of each 2-hour period; clear in color;
  k. Adding silver nitrate to the dialysate solution from the step k. to determine if the neutralizing antibody free of ammonium sulfate as confirmed by the absence of silver sulfate formation (precipitation);
  l. Separating the clear ammonium sulfate-free dialysate and;
  m. Collecting the neutralizing polyclonal antibody.

40. A method for inhibiting the proliferation of rapidly replication pathogenic substances within the cells of a patient or a biological system comprising administering at least one neutralizing antibody of Feature 32 to said patient or biological system.

41. The method of Feature 40 wherein the proliferation of rapidly replication of pathogenic substance is inhibited within the cells of a patient.

42. The method of Feature 41 wherein the patient is suffering from diseases and/or ailments from the group consisting of: viral infections; bacterial infections; fungal infections; parasitic infections and more specific diseases and/or ailments; such as as, AIDS; alzheimer's dementia; angiogenesis diseases; aphthour ulcers in AIDS patients; asthma; atopic dermatitis; psoriasis; basal cell carcinoma; benign prostatic hypertrophy; blood substitute; blood substitute in surgery patients; blood substitute in trauma patients; breast caner; cutaneous & metastatic; cachexia in AIDS; campylobacter infection; cancer; pnemonia; sexually transmitted diseases (STDs); cancer; viral diseases; candida albicians in AIDS and cancer; candidiasis in HIV infection; pain in cancer; pancreatic cancer; parkinson's disease; pentumoral brain edema; postoperative adhesions (prevent); proliferative diseases; prostate cancer, ragweed allergy; renal disease; restenosis; rheumatoid arthritis; allergies; rotavirus; infection scalp psoriasis; septic shock; small-cell lung cancer, solid tumors; stroke; thrombosis; type I diabetes; type I diabetes w/kidney transplants; type II diabetes; viseral leishmaniasis; malaria; periodontal or gum disease; carica rhythm disorders; central nervous system diseases; central nervous system disorders; cervical dystoma (spasmodic torticollis); choridal neovascularization; chronic hepatitis A, B and C; colitis associated with antibitotics; colorectal caner; coronary artery thrombosis; crytosporidiosis in AIDS; cryptosporidium parvum diarrhea in AIDS; cystic fibrosis; cytomegalovirus disease; depression; solid phobias; panic disorder; diabetic complications; diabetic eye disease; diarrhea associated with antibiotics; erectile dysfunction; genital herpes; graft-vs host disease in transplant patients; growth hormone neutralization after cardiac bypass; hepatocellular carcinoma; HIV; HIV infection; Huntington's disease; CNS diseases; hypercholesterolemia; hypertension; inflammation; inflammation and angiogensis; inflammation in cardiopulmonary bypass; influenza; migraine head ache; interstitial cystitis; contagiosum in AIDS; multiple sclerosis; neoplastic meningitis from solid tumors; non-small cell lung cancer; organ transplant rejection; osteoarthritis; rheumatoid arthritis; osteposoris; drug addiction; shock; ovarian cancer; Amebiasis; Babesiasis; Chagas' disease (Trypanosoma cruzi) Cryptosporidiosis; Cysticercosis; Fascioliasis; Filariasis; Echinococcosis; Giardiasis; Leishmaniasis; Malaria; Paragonimiasis; Pneumocystosis; Schistosomiasis; Strongylodiasis; Toxocariasis; Toxoplamosis; Trichinellosis; Trichomoniasis; yeast infection; stomach ulcers, sickle cell disease, obesity, burn wounds, skin cancer, skin burn, pulmonary disease, alzheimer's disease, heart disease, juvenile rheumatoid arthritis, scleroderma, bad breath, body odor, asthma, pulmonary disease, enteric disease, reflux, temporormandibular joint dysfunction, gallstones, cerebral palsy, prostate cancer, motion sickness, kidney stones, Lou Gerhig disease, infertility, erectile dysfunction, food poisoning, and pain, and combinations thereof.

43. The method of treating a patient or biological system in need thereof, comprising the steps of (1) treating said mammal or system according to the method of Feature 41 and (2) a therapeutically effective amount of salt of an alpha-keto carboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyi, halo, dihalo, or ethoxy on the phenyl right); adamantyl; phenyl; naphthyl; substituted phenyl or substituted naphthyl (wherein the ring is mono-, di-, or trisubstitued and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid, in an amount sufficient to inhibit proliferation of rapidly proliferating abnormal mammalian cells and enhancing the phosphorylation potential within the cells of a mammal or a biological system in order to prevent the deterioration or promote the restoration and preservation of normal cell functions, by releasing separate and sequential dosages of ingredients.

44. A vaccine produced from a neutralizing antibody prepared in accordance with Feature 32.

45. A vaccine prepared in accordance with Feature 44 to prevent the occurrence in patients of diseases and/or aliments comprising viral infections; bacterial infections; fungal infections; parasitic infections and more specific diseases and/or ailments; such as, AIDS; alzheimer's dementia; angiogenesis diseases; aphthour ulcers in AIDS patients; asthma; atopic dermatitis; psoriasis; basal cell carcinoma; benign prostatic hypertrophy; blood substitute; blood substitute in surgery patients; blood substitute in trauma patients; breast cancer; cutaneous & metastatic; cachexia in AIDS; campylobacter infection; cancer; pnemonia; sexually transmitted diseases (STDs); cancer; viral diseases; candida albicians in AIDS and cancer; candidiasis in HIV infection; pain in cancer; pancreatic cancer; parkinson's disease; peritumoral brain edema; postoperative adhesions (prevent); proliferative diseases; prostate cancer; ragweed allergy; renal disease; restenosis; rheumatoid arthritis; allergies; rotavirus; infection scalp psoriasis; septic shock; small-cell lung cancer, solid tumors; stroke; thrombosis; type I diabetes; type I diabetes w/kidney transplants, type IT diabetes; viseral leishmaniasis; malaria; periodontal or gum disease; cardica rhythm disorders; central nervous system diseases; central nervous system disorders; cervical dystonia (spasmodic torticollis); choridal neovascularization; chronic hepatitis A, B and C; colitis associated with antibiotics; colorectal cancer; coronary artery thrombosis; cryptosporidiosis in AIDS; cryptosporidium parvum diarrhea in AIDS; crystic fibrosis; cytomegalovirus disease; depression; social phobias; panic disorder; diabetic complications; diabetic eye disease; diarrhea associated with antibiotics; erectile dysfunction; genital herpes; graft-vs host disease in transplant patients; growth hormone neutralization after cardiac bypass; hepatocelluar carcinoma; HIV; IRV infection; huntington's disease, CNS diseases; hypercholesterolemia; hypertension; inflammation; inflammation and angiogenesis; inflammation in cardiopulmonary bypass; influenza; migraine head ache; interstitial cystitis; kaposi's sarcoma; kaposi's sarcoma in AIDS; lung cancer; melanoma; molluscum contagiosum in AIDS; multiple sclerosis; neoplastic meningitis from solid tumors; nonsmall cell lung cancer; organ transplant rejection; osteoarthritis; rheumatoid arthritis; osteoporosis; drug addiction; shock; ovarian cancer; Amebiasis; Babesiasis; Chagas' disease (Trypanosoma cruzi) Cryptosporidiosis; Cysticercosis; Fascioliasis; Filariasis; Echinococcosis; Giardiasis; Leishmaniasis; Malaria; Paragonimiasis; Pneumocystosis; Schistosomiasis; Strongylodiasis; Toxocariasis; Toxoplasmosis; Trichinellosis; Trichomoniasis; yeast infection; stomach ulcers, sickle cell disease, obesity, burn wounds, skin cancer, skin burn, pulmonary disease, alzheimer's disease, heart disease, juvenile rheumatoid arthritis, sclerodema, bad breath, body odor, asthma, pulmonary diseases, enteric diseases, reflux, temporomandiibular joint dysfunction, gallstones, cerebral palsy, prostate cancer, motion sickness, kidney stones, Lou Gerhig disease, infertility, erectile dysfunction, food poisoning, and pain, and combinations thereof.

46. A method for treating or preventing the onset of arteriosclerotic cardiovascular disease caused by intercellular cholesterol and-enching the phosphorylation potential within the normal cells of a mammal or a biological system in order to prevent and/or ameliorate deterioration or promote the restoration and preservation of normal cell functions comprising, administering concurrently together or by separate and sequential dosage, to the cells of a mammal in need there of or delivering to a biological system a pharmaceutical composition comprising a salt of an alpha-keto carboxylic acid having the formula R-C(0)(CO)OM wherein R is alkyl of 1-12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha-carbon atom or the substituent is methyl, dimethyl, halo, dihalo, or ethoxy on the phenyl ring); adamantyl; phenyl; naphyl; substituted phenyl or substituted naphthyl wherein the ring is mono-, di-, trisubstitued and the substituants are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

47. The method in accordance with Feature 46 wherein said cation is an alkali or alkaline earth metal.

48. The method in accordance with Feature 47 wherein the alkali metal is sodium.

49. The method in accordance with Feature 48 wherein R is an alkyl group containing 1 to 12 carbon atoms.

50. The method in accordance with Feature 49 wherein the alkyl group is methyl.

51. A method for enhancing the phosphorylation potential within the cells of a mammal in order to prevent and/or ameliorate the deterioration or promote the restoration and preservation of normal cell functions comprising administering to a mammal in need thereof a pharmaceutical composition containing as an active ingredient thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted naphthyl (wherein the ring mono-, di-, or trisubstitued and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

52. The method in accordance with Feature 51 wherein said cation is an alkali or alkaline earth metals.

53. The method in accordance with Feature 52 wherein the alkali metal is sodium.

54. The method in accordance with Feature 53 wherein R is an alkyl group containing 1 to 12 carbon atoms.

55. The method in accordance with Feature 54 wherein the alkyl group is methyl.

56. The method of Feature 56 wherein the proliferation of rapidly replication of pathogenic substance is inhibited within the cells of a patient.

57. The method of Feature 56 wherein the patient is suffering from diseases and/or ailments from the group consisting of: viral infections; bacterial infections; fungal infections; parasitic infections and more specific diseases and/or ailments; such as as, AIDS; alzheimer's dementia; angiogenesis diseases; aphthour ulcers in AIDS patients; asthma; atopic dermatitis; psoriasis; basal cell carcinoma; benign prostatic hypertrophy; blood substitute; blood substitute in surgery patients; blood substitute in trauma patients; breast cancer; cutaneous & metastatic; cachexia in AIDS; campylobacter infection; cancer; pnemonia; sexually transmitted diseases (STDs); cancer; viral diseases; candida albicians in AIDS and cancer; candidiasis in HIV infection; pain in cancer; pancreatic cancer; parkinson's disease; pentumoral brain edema; postoperative adhesions (prevent); proliferation diseases; prostate cancer; ragweed allergy; renal disease; restenosis; rheumatoid arthritis; allergies; rotavirus; infection scalp psoriasis; septic shock; small-cell lung cancer, solid tumors; stroke; thrombosis; type I diabetes; type I diabetes w/kidney transplants; type II diabetes; viseral leishmaniasis; malaria; periodontal or gum disease; cardiac rhythm disorders; central nervous system diseases; central nervous system disorders; cervical dystoma (spasmodic torticollis); choridal; neovascularization; chronic hepatitis A, B and C; colitis associated with antibiotics; colorectal cancer; coronary artery thrombosis; cyrtosporidiosis in AIDS; cryptosporidium parvum diarrhea in AIDS; cystic fibrosis; cytomegalovirus disease; depression; social phobias; panic disorder, diabetic complications; diabetic eye disease; diarrhea associated with antibiotics; erectile dysfunction; genital herpes; graft-vs host disease in transplant patients; growth hormone neutralization after cardiac bypass; hepatocellular carcinoma; HIV; HIV infection; Huntington's disease; CNS diseases; hypercholesterolemia; hypertension; inflammation; inflammation and angiogensis; inflammation in cardiopulmonary bypass; influenza; migraine head ache; interstital cystitis; contagiosum in AIDS; multiple sclerosis; neoplastic meningitis from solid tumors; non-small cell lung cancer; organ transplant rejection; osteoarthritis; rheumatoid arthritis; osteoporosis; drug addiction; shock; ovarian cancer; Amebiasis; Babesiasis; Chagas' disease (Trypanosoma cruzi) Cryptosporidiosis; Cysticercosis; Fascioliasis; Filariasis; Echinococcosis; Giardiasis; Leishmaniasis; Malaria; Paragonimiasis; Pneumocystosis; Schistososmiasis; Strongylodiasis; Toxocariasis; Toxoplasmosis; Trichinellosis; Trichomoniasis; yeast infection; stomach ulcers, sickle cell disease, obesity, burn wounds, skin cancer, skin burn, pulmonary disease, alzehimer's disease, heart disease, juvenile rheumatoid arthritis, scleroderma, bad breath, body odor, asthma, pulmonary diseases, enteric diseases, reflux, temporomandibular joint dysfunction, gallstones, cerebral palsy, prostate cancer, motion sickness, kidney stoned, Lou Gerhig disease, infertility, erectile dysfunction, food poisoning, and pain, and combinations thereof.

58. A method for enhancing the phosphorylation potential within the cells of a mammal in order to prevent and/or ameliorate the deterioration or promote the restoration and preservation of normal cell functions comprising administering to a mammal in need thereof a perenteral fluid containing as an active ingredient thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

59. A method according to Feature 58 wherein the perenteral fluid is selected from the group comprising total perenteral nutritional fluids; kidney and peritoneal dialyses fluids; volume and plasma expanding fluids; pyruvate/acetate near-isotonic solutions; lactase/acetate-free pyruvate isotonic-solutions; normal saline solutions; hemoglobin-substitute containing solutions; vitamin supplement product; and cardioplegic solutions.

60. A method according to Feature 58 wherein the amount of active ingredient is effective in reducing and/or ameliorating intracellular acidosis.

61. A method according to Feature 58 wherein the amount of active ingredient is effective in neutralizing hydrogen peroxide through hydrogen peroxide-alpha-ketocarboxylate interaction to inhibit the formation of toxic-free radicals.

62. A method for exchanging the phosphorylation potential within the cells of a mammal in order to prevent and/or ameliorate the deterioration or promote the restoration and preservation of normal cell functions comprising administering to a mammal in need thereof a rehydration fluid, which may contain electrolyte balances, contain as an active ingredient thereof a salt of an alphaketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 atoms; benzyl; substituted benzyl (wherein the substituent is methyl, phenyl on the alpha carbon atom or the substituent in methyl, dimethyl, halo, dihalo, or ethoxy on the phenyl ring); adamantyl; phenyl; naphthyl; substituted phenyl or substituted napthyl (wherein the ring is mono-, di-, or trisubstitued and the substitutents are alkyl of Ito 4 carbon atoms, halo, alkoxy of 1 to 4 carbon atoms, phenoxy, trihalomethyl, dimethylamino, diethylamino, and M is a certain alone or in combination with nicatinamide, creatine and/or an aminoacid.

63. A method according to Feature 62 wherein the rehydration fluid contains electrolyte balances.

64. A method for enhancing the phosphorylation potential within the cells of a mammal in order to prevent and/or ameliorate the deterioration or promote the restoration and preservation of normal cell functions comprising administering a mammal in need thereof a topical composition containing as an active ingredient thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbons atoms, halo, alkoxy of 1 to 4 carbon atoms, phenoxy, trihalomethyl, dimethylamino, diethylamino, and M is a cation alone or in combination with nicatinamide, creatine and/or an amino acid.

65. A method according to Feature 64 wherein the topical composition is selected from the group comprising medicinal soaps; medicinal shampoos; sunscreens; medicinal ointments; vitamin capsules; dentrifice; mouthwash; douche solutions; and medicinal baths.

66. A method for enhancing the phosphorylation potential within the cells of a mammal in order to present the deterioration or promote the restoration and preservation of normal cell functions comprising administering to a mammal in need thereof a pharmaceutical composition selected from the group comprising an antibiotic and antiplogistic containing as an active ingredient thereof a salt of an alpha-ketocarboxylic acid having the formula R-C(0)(CO)

OM wherein R is alkyl of 1 to 12 carbon atoms; substituted alkyl of 1 to 12 carbon atoms, cyloalkyl of 3 to 10 carbon atoms, within the alkylene chain, halogen amino, alhylamino of 1 to 4 carbon atoms dialkylamino of 1 to 4 carbon atoms in each alkyl, alkenyl of 2 to 6 carbon atoms; alkynyl of 3-to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphythyl; substituted phenyl or substituted napthyl (wherein the ring is mono-, di-, or trisubstituted and the substituents are alkyl of 1 to 4 carbons atoms, halo, alkoxy of 1 to 4 carbon atoms, phenoxy, trihalomethyl, dimethylamino, diethylamino, and M is a cation alone or in combination with nicatinamide, creatine and/or an aminoacid.

67. The method in accordance with Feature 66 wherein said composition is administered by intramuscular injection.

68. The method in accordance with Feature 67 wherein said composition is an antibiotic.

69. The method in accordance with Feature 68 wherein said composition is an antiphylogistic.

70. A method for enhancing the phosphorylation potential within the cells of a mammal in order to prevent and/or ameliorate the deterioration or promote the restoration and preservation of normal cell functions comprising administering to a mammal in need thereof a pharmaceutical composition for the treatment of local skin disorders, selected from the group comprising an antibiotic and antiphlogiotic having as an active ingredient thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 atoms; benzyl; substituted benzyl (wherein the substituent is methyl, phenyl on the alpha carbon atom or the substituent in methyl, dimethyl, halo, dihalo, ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

71. A method for enhancing the phosphorylation potential within the cells of a mammal in order to prevent and/or ameliorate the deterioration or promote the restoration and preservation of normal cell functions comprising administering to a mammal in need thereof an aerosolized pharmaceutical composition containing as an active ingredient thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, (carboxyalkylene of 1 to 20 carbon atoms within the alkylene chains, halogen amino, alkylamino of 1 to 4 carbon atoms, dialkylamino of 1 to 4 carbon atoms in each alkyl group or phenyl); alkenyl of 2 to 6 carbon atoms; alkynyl of 3 to 6 atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphythyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with a bronchodilating agent.

72. A method in accordance with Feature 71 resulting in the amelioration or prevention of the onset of abnormal respiratory conditions caused by a reactive airway disease.

73. A method in accordance with Feature 72 wherein said reactive airway disease is selected from the group comprising asthma and bronco-pulmony dyplasia.

74. A method for enhancing the phosphorylation potential within the cells of a mammal in order to prevent and/or ameliorate the deterioration or promote the restoration and preservation of normal cell functions comprising perfusion of a mammalian organ in need thereof with pharmaceutical composition containing as an active ingredient thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atoms or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an amino acid.

75. The method in accordance with Feature 74 wherein said mammalian organ is selected from the group comprising heart, liver, kidney, brain, spleen vessels, arteries, endothelium, pancreas and glands.

76. A method for enhancing the phosphorylation potential within bacterial or viral cells in culture or cloning media in order to prevent and/or ameliorate the deterioration or promote the restoration and preservation of normal cell functions comprising adding to the incubation solution for said cells a pharmaceutical composition containing as an active ingredient thereof a salt of an alpha ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

77. A method for enhancing the phosphorylation potential within the cells of a mammal in order to prevent and/or ameliorate the deterioration or promote the restoration and preservation of normal cell functions thereby enhancing physical endurance or refreshment comprising administering to a mammal in need thereof a food product containing a pharmaceutical composition having as an active ingredient there of a salt of an alpha-ketocarboxylic acid having the formal R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

78. The method in accordance with Feature 77 wherein said food product is a beverage drink.

79. The method in accordance with Feature 78 wherein said food product comprises rice, meat, bread, pasta, fish, fruit, poultry, vegetables and a confectionery food.

80. The method in accordance with Feature 79 wherein said food product is selected from the group comprising candies and pastries.

81. A method for enhancing the phosphorylation potential within the cells of a mammal in order to prevent and/or ameliorate the deterioration or promote the restoration and preservation of normal cell functions comprising administering to a mammal in need thereof a pharmaceutical composition containing (1) a thiamine (B1) vitamin capsule and (2) a therapeutically-effective amount of a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

82. A composition of matter for enhancing the phosphorylation potential within the cells of a mammal of a biological system in order to prevent and/or ameliorate the deterioration or promote the restoration and preservation of normal cell functions comprising a therapeutically effective amount of a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

83. A composition according to Feature 80 wherein said salt of an alpha-ketocarboxylic acid is present in combination with nicatinamide, creatine and/or an aminoacid.

84. An augmented composition for inhibiting the proliferation of rapidly replication abnormal mammalian cells and enhancing the phosphorylation potential within the normal cells of a mammal or a biological system in order to prevent and/or ameliorate the deterioration or promote the restoration and preservation of normal cell functions within comprises:

(1) a therapeutic cell normalizing composition which comprises: a therapeutically effective amount of a salt of an alpha-keto carboxylic acid having the formula R-C(0)(CO)OM wherein R is alkyl of 1 to 12 carbon atoms; substituted alkyl of 1 to 12 carbon atoms; cyloalkyl of 3 to 10 carbon atoms; alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl 6 halo, dihalo; or ethoxy on the phenyl ring); adamantyl; phenyl; napthyl; substituted phenyl or substituted napthyl (wherein the ring is mono-, di, or trisubstituted and the substituents are alkyl of 1 to 4 carbon atoms, halo, alkoxy to 1 to 4 carbon atoms, phenoxy, trihalomethyl, dimethylamino, diethylamino, and M is a cation alone or in combination with nicatinamide, creatine and/or an aminoacid; and (2) a medicament useful for treating injured cells.

85. The augmented composition according to Feature 82 wherein the medicament is selected from the group consisting of a antibacterial agents, antiviral agents, antifungal agents, antimicrobial agents, antiprotozoan agents, antipollen agents, antivenom agents, antiparasitic agents, antiyeast agents, mmunostimulating agents, antikeratolytic agents, antiinflammatory agents, acne treating agents, sunscreen agents, dermatological agents, antihistamine agents, bioadhesvie agents, respiratory bursting inhibitors, inhibitors of prostaglandin synthesis, antiseptic agents, anesthetic agents, cell nutrient media, bunn relief medications, sun burn medications, insect bite and sting medications, wound cleaners, wound dressings scar reducing agents, glucose (dextrose), creatine, aminoacids, medicinal soaps, medicinal shampoos, medicinal ointment, vitamin capsules, dentrifice agents, mouthwashing agents, douche solution, anti-cancer agents, medicinal baths, antibiotics, antitumor agents, anitpyrectics analgesics, antituissives, expectorants, sedatives, muscle relaxants, antiulcer agents, antidepressants, antiallergic drugs, cardiotonics, vasodilators, factors, narcotic antagonists, analgesics, spermicidal compounds, gastrointestinal therapeutic agents, protease inhibitors, and insulins.

86. A perenteral fluid useful for enhancing the phosphorylation potential within the cells of a mammal in order to prevent and/or ameliorate the deterioration or promote the restoration and preservation of normal cell functions comprising a therapeutically-effective amount of a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substituents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

87. A composition according to Feature 86 wherein the parenteral fluid is selected from the group comprising total parenteral nutritional fluids; kidney and peritoneal dialyses fluids; volume and plasma expanding fluids; pyruvate/acetate near-isotonic solutions; lactate/acetate-free pyruvate isotonic solutions; normal saline solutions; hemoglobin-substitute containing solutions; vitamin supplement product; and cardioplegic solutions.

88. A rehydration fluid, which may contain electrolyte balances, useful for enhancing the phosphorylation potential within the cells of a mammal in order to prevent and/or ameliorate the deterioration or promote the restoration and preservation of normal cell functions comprising a therapeutically-effective amount of a salt of an alpha-ketocarboxylic acid having the formula R-C(0)(CO)OM wherein R is alkyl of 1 to 12 carbon atoms; substituedt alkyl of 1 to 12 carbon atoms, cyloalkyl of 3 to 10 carbon atoms, alkenyl of 2 to 6 carbon atoms; alkynyl of 3 to 6 atoms; benzyl; substituted benzyl (wherein the subsistent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

89. A composition according to Feature 88 wherein the rehydration fluid contains electrolyte balances.

90. A medicinal composition useful for enhancing the phosphorylation potential within the cells of a mammal in order to prevent and/or ameliorate the deterioration or promote the restoration and preservation of normal cell functions comprising a therapeutically effective amount of thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphythyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

91. A composition according to Feature 90 is selected from the group comprising medicinal soaps; medicinal shampoos; sunscreens; medicinal ointments; vitamin capsules; dentrifice; mouthwash; douche solutions; and medicinal baths.

92. An antibiotic or antiphlogistic composition useful for enhancing the phosphorylation potential within the cells of a mammal in order to prevent and/or ameliorate the deterioration or promote the restoration and preservation of normal cell functions comprising a therapeutically effective amount of salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, within the alkylene chain, halogen amino, alkylamino of 1 to 4 carbon atoms dialkylamino of 1 to 4 carbon atoms in each alkyl, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphythyl; substituted phenyl or substituted napthyl (wherein the ring is mono-, di-, or trisubstituted and the substitutents are alkyl of 1 to 4 carbons atoms, halo, alkoxy of 1 to 4 carbon atoms, phenoxy, trihalomethyl, dimethylamino, diethylamino, and M is a cation alone or in combination with nicatinamide, creatine and/or an amino acid.

93. The composition according to Feature 92 wherein said composition is administered by intramuscular injection.

94. The composition according to Feature 92 wherein said composition is an antibiotic.

95. The method in accordance with Feature 92 wherein said composition is an antiphylogistic.

96. An aerosolized pharmaceutical composition for enhancing the phosphorylation potential within the cells of a mammal in order to prevent and/or ameliorate the deterioration or promote the restoration and preservation of normal cell functions comprising a therapeutically effective amount of a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, (carboxyalkylene of 1 to 20 carbon atoms within the alkylene chain, halogen amino, alkylamino of 1 to 4 carbon atoms, dialkylamino of 1 to 4 carbon atoms in each alkyl group or phenyl); alkenyl of 2 to 6 carbon atoms; alkynyl of 3 to 6 atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substituents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid, or further in combination with a bronchodilating agent.

97. A perfusion fluid for enhancing the phosphorylation potential within the cells of a mammal in order to prevent and/or ameliorate the deterioration or promote the restoration and preservation of normal cell functions comprising a therapeutically effective amount of a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

98. An incubation solution for enhancing the phosphorylation potential within bacterial or viral cells in culture or cloning media in order to prevent and/or ameliorate the deterioration or promote the restoration and preservation of normal cell functions comprising a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

99. A food product for enhancing the phosphorylation potential within the cells of a mammal in order to prevent and/or ameliorate the deterioration or promote the restoration and preservation of normal cell functions thereby enhancing physical endurance or refreshment comprising a pharmaceutical composition having as an active ingredient thereof a salt of an alpha-ketocarboxylic acid having the formula R-C(0)(CO)OM wherein R is alkyl of 1 to 12 carbon atoms; substituted alkyl of 1 to 12 carbon atoms; cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is method, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

100. The food product in accordance with Feature 99 wherein said food product is a beverage drink.

101. The food product in accordance with Feature 99 wherein said food product comprises meat, bread, pasta, fish, fruit, poultry, vegetables and a confectionery food.

102. The food product in accordance with Feature 99 wherein said food product is selected from the groups comprising candies and pastries.

103. A vitamin supplement product for enhancing the phosphorylation potential within the cells of a mammal in order to prevent and/or ameliorate the deterioration or promote the restoration and preservation of normal cell functions hereby enhancing physical endurance or refreshment comprising a therapeutically effective amount of a slat of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substituents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

104. A method for preventing and/or ameliorating the adverse cardiovascular effects of a massive complement activation in a mammal comprising administering to a mammal in need thereof a pharmaceutically-effective amount of an essentially non-toxic cardiac adenosine A1 receptor blocking agent.

105. The method in accordance with Feature 103 wherein the receptor blocking agent is Cyclopentyl-diprophyl xanthine.

106. A composition for preventing and/or ameliorating the adverse cardiovascular effects of a massive complement activation and enhancing the phosphorylation potential within the cells of a mammal or a biological system in order to prevent and/or reduce the deterioration or promote the restoration and preservation of normal cell functions comprising (1) at least one essentially nontoxic cardiac adenosine A1 receptor blocking agent and (2) a therapeutically effective amount of a salt of an alpha-ketocarboxylic acid having the formula R-C(0)(CO)OM wherein R is alkyl of 1 to 12 carbon atoms; substituted alkyl of 1 to 12 carbon atoms; cyloalkyl of 3 to 10 carbon atoms; alkenyl of 2 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstituted and the substituents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an amino acid.

107. A composition of Feature 106 wherein the essentially nontoxic cardiac adenosine A1 receptor blocking agent is cyclopentyl-diprophyl xanthine.

108. A method for preventing and/or ameliorating the adverse cardiovascular effects of a massive complement activation and enhancing the phosphorylation potential within the normal cells of a mammal or a biological system in order to prevent and/or reduce the deterioration or promote the restoration and preservation of normal cell functions comprising administering concurrently or by separate and sequential dosage, to the mammal in need thereof or delivering to a biological system a pharmaceutical composition comprising (1) an essentially nontoxic cardiac adenosine A1 receptor blocking agent (2) a salt of an alpha-keto carboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms, alkynyl of 3 to 6 carbon atoms; benzyl ; substituted benzyl (wherein the substituent is methyl, phenyl on the alpha carbon atom or the substituent is methyl, dimethyl, halo, dihalo, or ethoxy on the phenyl; ring); adamantyl; phenyl; naphthyl; substituted phenyl or substituted naphthyl wherein the ring is mono-, di or trisubstituted and the substituents are alkyl or 1 to 4 carbon atoms, halo alkoxy of 1 to 4 carbon atoms, phenoxy, trihalomethyl, dimethylamino diethylamino, and M is a cation, alone or in combination with nicatinamide, creatine and/or an amino acid and (3) a combination thereof.

While the invention has been described in terms of its preferred embodiments, those skilled in the art will recognize that the invention can be practiced with modification within the scope of the appended claims.

Having thus described the invention, what is claimed as new and desired to be secured by Letters Patent is as follows:

1. A method for enhancing the phosphorylation potential within the cells of a mammal in order to retard and/or ameliorate the deterioration or promote the restoration and preservation of normal cell functions comprising administering to a mammal in need thereof a pharmaceutical composition containing as an active ingredient thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 of 10 carbon atoms, alkynyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide and creatine.

2. The method in accordance with claim 1 wherein said cation is an alkali or alkaline earth metal.

3. The method in accordance with claim 2 wherein the alkali metal is sodium.

4. The method in accordance with claim 3 wherein R is an alkyl group containing 1 to 12 carbon atoms.

5. The method in accordance with claim 4 wherein the alkyl group is methyl.

6. The method of claim 1 wherein the patient is suffering from diseases and/or ailments from the group consisting of: viral infections; bacterial infections; fungal infections; parasitic infections and more specific disease and/or ailments; such as as, AIDS; alzheimer's dementia; angiogenesis diseases; aphthous ulcers in AIDS patients; asthma; atopic dermatitis; psoriasis; basal cell carcinoma; benign prostatic hypertrophy; blood substitute; blood substitute in surgery patients; blood substitute in trauma patients; breast cancer; cutaneous & metastatic; cachexia in AIDS; campylobacter infection; cancer; pnemonia; sexually transmitted diseases (STDs); cancer; viral diseases; candida albicains in AIDS and cancer; candidiasis in HIV infection; pain in cancer; pancreatic cancer; parkinson's disease; pentumoral brain edema; postoperative adhesions (prevent); proliferative diseases; prostate cancer, ragweed allergy; renal disease; restenosis; rheumatoid arthritis; allergies; rotavirus; infection scalp psoriasis; septic shock; small-cell lung cancer, solid tumors; stroke; thrombosis; type I diabetes; type I diabetes w/kidney transplants; type II diabetes; viseral leishmaniasis; malaria; periodontal or gum disease; cardiac rhythm disorders; central nervous system diseases; central nervous system disorders; cervical dystoma (spasmodic torticollis); choridal neovascularization; chornic hepatitis A, B and C; colitis associated with antibiotics; colorectal cancer; coronary artery thrombosis; crytosporidliosis in AIDS; cyrptosporidium parvum diarrhea in AIDS; cystic fibrosis; cytomegalovirus disease; depression; social phobias; panic disorder, diabetic complications; diabetic eye disease; diarrhea associated with antibiotics; erectile dysfunction; genital herpes; graft-vs host disease in transplant patients; growth hormone neutralization after cardiac bypass; hepatocellular carcinoma; HIV; HIV infection; Huntington's disease; CNS diseases; hypercholesterolemia; hypertension; inflammation; inflammation and angiogensis; inflammation in ccardiopulmonary bypass; influenza; migraine head ache; interstitial cystitis; contagiosum in AIDS; multiple sclerosis; neoplastic meningitis from solid tumors; non-small cell lung cancer; organ transplant rejection; osteoarthritis; rheumatoid arthritis; osteoporosis; drug addition; shock; ovarian cancer; Amebiasis; Babesiasis; Chagas' disease (Trypanosoma cruzi) Cryptosporidiosis; Cysticercosis; Fascioliasis; Filariasis; Echinococcosis; Giardiasis; Leishmeniasis; Malaria; Paragonimiasis; Pneumocystosis; Schistosomiasis; Strongylodiasis; Toxocariasis; Toxoplasmois; Trichinellosis; Trichomoniasis; yeast infection; stomach ulcers, sickle cell disease, obesity, burn wounds, skin caner, skin bum, pulmonary disease, alzheimer's disease, heart disease, juvenile rheumatoid arthritis, scleroderma, bad breath, body odor, asthma, pulmonary diseases, enteric diseases, reflux, temporomandibular joint dysfunction, gallstones, cerebral palsy, prostate cancer, motion sickness, kidney stones, Lou Gerhig disease, infertility, erectile dysfunction, food poisoning, and pain, and combinations thereof.

7. A method for enhancing the phosphorylation potential within the cells of a mammal in order to retard and/or ameliorate the deterioration or promote the restoration and preservation of normal cell functions comprising perfusion of a mammalian organ in need thereof with pharmaceutical composition containing as an active ingredient thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substituents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an amino acid.

8. The method in accordance with claim 7 wherein said mammalian organ is selected from the group comprising heart, liver, kidney, brain, spleen vessels, arteries, endothelium, pancreas and glands.

9. A method for enhancing the phosphorylation potential within the cells of a mammal in order to retard and/or ameliorate the deterioration or promote the restoration and preservation of normal cell functions thereby enhancing physical endurance or refreshment comprising administering to a mammal in need thereof a food product containing a pharmaceutical composition having as an active ingredient thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

10. The method in accordance with claim 9 wherein said food product is a beverage drink.

11. The method in accordance with claim 10 wherein said food product comprises rice, meat, bread, pasta, fish, fruit, poultry, vegetables and a confectionery foods.

12. The method in accordance with claim 11 wherein said food product is selected from the group comprising candies and pastries.

13. A composition of matter for enhancing the phosphorylation potential within the cells of a mammal or a biological system in order to retard and/or ameliorate the deterioration or promote the restoration and preservation of normal cell functions comprising a therapeutically effective amount of a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substituents are alkyl of 1 to 4 carbon atoms, halo, alkoxy of 1 to 4 carbon atoms, phenoxy, trihalomethyl, dimethylamino, diethyamino, and M is a cation alone or in combination with nicatinamcie and creatine.

14. A composition according to claim 13 wherein said salt of an alpha-ketocarboxylic acid is present in combination with nicatinamide, creatine and/or an aminoacid.

15. A food product for enhancing the phosphorylation potential within the cells of a mammal in order to retard and/or ameliorate the deterioration or promote the restoration and preservation of normal cell functions thereby enhancing physical endurance or refreshment comprising a pharmaceutical composition having as an active ingredient thereof a salt of an alpha-ketocarboxylic acid having the formula R-C(0)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substituents are alkyl of 1 to 4 carbon atoms, halo, alkoxy of 1 to 4 carbon atoms, phenoxy, trihalomethyl, dimethylamino, diethylamino, and M is a cation alone or in combination with nicatinamide, creatine and/or an aminoacid.

16. The food product in accordance with claim 15 wherein said food product is a beverage drink.

17. The food product in accordance with claim 15 wherein said food product comprises meat, bread, pasta, fish, fruit, poultry, vegetables and a confectionery food.

18. The food product in accordance with claim 15 wherein said food product is selected from the group comprising candies and pastries.

19. A method in accordance with claim 1, wherein the composition is a parenteral fluid.

* * * * *